(12) United States Patent
Chamuleau et al.

(10) Patent No.: US 8,921,108 B2
(45) Date of Patent: Dec. 30, 2014

(54) DIFFERENTIATED HUMAN LIVER CELL CULTURES AND THEIR USE IN BIOARTIFICIAL LIVER SYSTEMS

(75) Inventors: Robert Antoine François Marie Chamuleau, Bussum (NL); Ruurdtje Hoekstra, Weesp (NL); Gerardus Adrianus Antonius Nibourg, Amsterdam (NL)

(73) Assignee: Academisch Ziekenhuis Bij de Universiteit van Amsterdam, Amsterdam (NL)

( * ) Notice: Subject to any disclaimer, the term of this patent is extended or adjusted under 35 U.S.C. 154(b) by 157 days.

(21) Appl. No.: 13/265,421

(22) PCT Filed: Apr. 21, 2010

(86) PCT No.: PCT/NL2010/050216
§ 371 (c)(1),
(2), (4) Date: Jan. 23, 2012

(87) PCT Pub. No.: WO2010/123357
PCT Pub. Date: Oct. 28, 2010

(65) Prior Publication Data
US 2012/0111795 A1 May 10, 2012

(30) Foreign Application Priority Data
Apr. 21, 2009 (EP) .................... 09158368

(51) Int. Cl.
*C12N 5/02* (2006.01)
*C12N 5/071* (2010.01)

(52) U.S. Cl.
CPC .......... *C12N 5/0671* (2013.01); *C12N 2500/32* (2013.01)
USPC ....................................... 435/375

(58) Field of Classification Search
CPC .................................................. C12N 5/067
USPC ............................................... 435/375
See application file for complete search history.

(56) References Cited

U.S. PATENT DOCUMENTS

2005/0064594 A1* 3/2005 Gripon et al. .................. 435/456

FOREIGN PATENT DOCUMENTS

WO 03/004627 A2 1/2003

OTHER PUBLICATIONS

Kanebratt Kajsa P et al.: "Evaluation of HepaRG cells as an in vitro model for human drug metabolism studies" Drug Metabolism and Disposition, vol. 36, No. 7, Jul. 2008, pp. 1444-1452, XP002547278 ISSN: 0090-9556.

Josse Rozenn et al.: "Long-term functional stability of human HepaRG hepatocytes and use for chronic toxicity and genotoxicity studies" Drug Metabolism and Disposition, vol. 36, No. 6, Jun. 2008, pp. 1111-1118, XP002547279, ISSN: 0090-9556.

Chamuleau Rafm et al.: "Which are the right cells to be used in a bioartificial liver?" Metabolic Brain Disease 200512 US, vol. 20, No. 4, Dec. 2005, pp. 327-335, XP002395892 ISSN: 0885-7490.

Schwartlander Ruth et al.: "Continuously microscopically observed and process-controlled cell culture within the SlideReactor: Proof of a new concept for cell characterization" Tissue Engineering, vol. 13, No. 1, Jan. 2007, pp. 187-196, XP002547280, ISSN: 1076-3279.

Fiegel Henning C et al.: "Hepatic tissue engineering: from transplantation to customized cell-based liver directed therapies from the laboratory" Journal of Cellular and Molecular Medicine, vol. 12, No. 1, Jan. 2008, pp. 56-66, XP002547281 ISSN: 1582-1838.

Poyck et al.: "Evaluation of a new immortalized human fetal liver cell line (cBAL111) for application in bioartificial liver" Journal of Hepatology, Munksgaard International Publishers, Copenhagen, DK, vol. 48, No. 2, Dec. 17, 2007, pp. 266-275, XP022478906, ISSN: 0168-8278.

Poyck Paul P C et al.: ."Functional and morphological comparison of three primary liver cell types cultured in the AMC bioartificial liver." Liver Transplantation : Official Publication of the American Association for the Study of Liver Diseases and the International Liver Transplantation Society Apr. 2007, vol. 13, No. 4, Apr. 2007, pp. 589-598, XP002547282, ISSN: 1527-6465.

Deurholt Tanja et al.: "Novel immortalized human fetal liver cell line, cBAL111, has the potential to differentiate into functional hepatocytes" BMC Biotechnology, vol. 9, Oct. 2009, XP21062965 ISSN: 1472-6750.

Poyck Paul P C et al.: "Expression of glutamine synthetase and carbamoylphosphate synthetase I in a bioartificial liver: Markers for the development of zonation in vitro" Cells Tissues Organs, vol. 188, No. 3, 2008, pp. 259-269, XP009133847 ISSN: 1422-6405, tables 2-3.

Nibourg G A A et al.: "Overexpression of Pregnane X Receptor in Hepatoma Cell Line HEPG2 Increases Its Potential for Bioartificial Liver Application" International Journal of Artificial Organs, vol. 32, No. 7, Jul. 2009, p. 396, XP009133846 & 36th Congress of the European-Society-Of-Artificial-Organs; Compiegne, France; Sep. 2-5, 2009 ISSN: 0391-3988.

International Search Report, dated Jun. 7, 2010, from corresponding PCT application.

Enosawa S. et al: "The significant improvement of survival times and pathological parameters by bioartificial liver with recombinant HepG2 in porcine liver failure model", 2006, Cell Transplantation, vol. 15, pp. 873-880.

Flendrig L. et al: "In vitro evaluation of novel bioreactor based on integral oxygenator and a spirally wound nonwoven polyester matrix for hepatocyte culture as small aggregates",1997, Journal of Hepatology, vol. 26, pp. 1379-1392.

(Continued)

Primary Examiner — Ruth Davis
(74) Attorney, Agent, or Firm — Young & Thompson

(57) ABSTRACT

The present invention concerns human hepatocyte cell line cultures and their use in bioartificial liver (BAL) systems. These systems are used to treat subjects suffering from liver failure to temporarily compensate for loss of hepatocellular function and generally comprise a bioreactor loaded with functional liver cells. Until now, it has been problematic to acquire cells with a broad spectrum metabolic functionality, resembling that of freshly isolated human hepatocytes, to the extent that they are in fact suitable for successful clinical BAL application The present inventors have managed to develop human hepatocyte cell line cultures that display broad-spectrum metabolic functionality such as to render them particularly suitable for effective clinical BAL application.

12 Claims, 2 Drawing Sheets

(56) References Cited

OTHER PUBLICATIONS

Hoekstra R. et al: "Increased reproducibility of quantitative reverse transcriptase—PCR", 2005, Analytical Biochemistry, vol. 340, pp. 376-379.

Hoekstra R. et al: "Assessment of in Vitro Applicability of Reversibly Immortalized NKNT-3 Cells and Clonal Derivatives", 2006, Cell Transplantation, vol. 15, pp. 423-443.

Kanai H. et al: "Thoughts and Progress", 2007, Artificial Organs, vol. 31, No. 2, pp. 148-170.

Kerkhove et al: "Assessment and improvement of liver specific function of the AMC-bioartificial liver", 2005, The Journal of Artificial Organs, vol. 28, No. 6, pp. 1-14.

Kerkhove et al: "Phase I clinical trial with the AMC-bioartificial liver", 2002, The Journal of Artificial Organs, vol. 25, No. 10, pp. 950-959.

Kosuge M. et al: "A comprehensive gene expression analysis of human hepatocellular carcinoma cell lines as components of a bioartificial liver using a radial flow bioreactor", 2007, Liver International, pp. 101-108.

Mavri-Damelin D. et al: "Cells for Bioartificial Liver Devices: The Human Hepatoma-Derived Cell Line C3A Produces Urea But Does Not Detoxify Ammonia", Feb. 2008, Biotechnology and Bioengineering, vol. 99, No. 3, pp. 644-651.

Nyberg S. et al "Primary Hepatocytes Outperform Hep G2 Cells as the Source of Biotrasformation Functions in a Bioartificial Liver", 1994, Annals of Surgery, vol. 220, No. 1, pp. 59-67.

Park & Lee: "Review: Bioartificial Liver Systems: Current Status and Future Perspective", 2005, Journal of Bioscience and Bioengineering, vol. 99, No. 4, pp. 311-319.

Poyck P. et al: "Evaluation of a new immortalized human fetal liver cell line 3 (cBAL111) for application in bioartificial liver", 2008, Journal of Hepatology, pp. 1-10.

Poyck P. et al: "Time-Related Analysis of Metabolic Liver Functions, Cellular Morphology, and Gene Expression of Hepatocytes Cultured in the Bioartificial Liver of the Academic Medical Center in Amsterdam (AMC-BAL)", 2007, Tissue Engineering, vol. 13, No. 6, pp. 1236-1245.

Ramakers C. et al: "Assumption-free analysis of quantitative real-time polymerase chain reaction (PCR) data", 2003, Neuroscience Letters, vol. 339, pp. 62-66.

Rozga J. & Demetriou A.: "Development and testing of Bioartifical Liver", 2000, The Hepatocyte Review, Kluwer Academic Publishers: Netherlands, pp. 543-559.

Saito M. et al: "Reconstruction of liver organoid using a bioreactor", Mar. 2006, World J Gastroenterol, vol. 12 No. 12, pp. 1881-1888.

Sgroi A. et al: "What Clinical Alternatives to Whole Liver Transplantation? Current Status of Artificial Devices and Hepatocyte Transplantation", Feb. 2009, Transplantation, vol. 87, No. 4, pp. 457-466.

Takahashi M. et al: "Double-Compartment Cell Culture Apparatus: Construction and Biochemical Evaluation for Bioartificial Liver Support", 2006, Cell Transplantation, vol. 15, pp. 945-952.

Tanja D. et al: "Novel immortalized human fetal liver cell line, cBAL111, has the potential to differentiate into functional hepatocytes", 2009, BMC Biotechnology, vol. 9, No. 89, pp. 1-15.

Wang N. et al: "Thoughts and Progress", 2005, Artificial Organs, vol. 29, No. 8, pp. 681-684.

* cited by examiner

DIFFERENTIATED HUMAN LIVER CELL CULTURES AND THEIR USE IN BIOARTIFICIAL LIVER SYSTEMS

FIELD OF THE INVENTION

The present invention concerns the field of bioartificial liver (BAL) systems. Such BAL systems are used to treat subjects suffering from liver failure to temporarily compensate for loss of hepatocellular function and generally comprise a bioreactor loaded with functional liver cells. The present invention, in particular, concerns human liver cells that are particularly suitable for use in these BAL systems. The present invention furthermore provides new BAL systems, configured to allow for these human liver cells to be utilized to their full potential. Furthermore, the present invention concerns the use of the aforementioned human liver cells and the aforementioned BAL systems for treating subjects suffering from a condition resulting in loss of hepatocellular function, such as acute liver failure, end-stage liver disease or acute-on-chronic liver disease.

BACKGROUND OF THE INVENTION

Chronic liver disease is responsible for over 1.4 million disability adjusted life years annually and ranks in the United States among the top 7 disease-related causes of death between the age of 25 and 64 years. For end-stage liver failure, orthotopic liver transplantation remains the current treatment of choice. However, patients suffering from acute or acute-on-chronic liver failure may benefit from temporary extracorporeal artificial liver support used to tide them over until transplantation or to allow regeneration of their own liver to occur.

Bioartificial liver (BAL) systems seem to be a promising solution for this purpose. These systems allow for extracorporeal blood (plasma) treatment relying on functional liver cell cultures for detoxification and synthetic function. Over the last 2 decades, many BAL systems have been devised, only some of which systems have been applied in a clinical (pilot) setting. BALs are based on a bioreactor facilitating functional liver cells and can be employed to compensate for the loss of hepatocellular function by perfusing the reactor with the subject's blood plasma. Some BAL systems comprise a bioreactor in combination with a non-biological detoxification modality, such as a charcoal column or a bilirubin column (so called hybrid systems). For a more complete understanding of existing BAL technology, Park and Lee[1] or Sgroi et al.[2] may be referred to, providing comprehensive overviews of the different types of reactors and the different system configurations developed by various groups up to 2009.

The cell source employed in the BAL bioreactor should exhibit high hepatic functionality. Although the pathogenesis of hepatic encephalopathy (HE), one of the major causes of death of ALF, is multifactorial, it is generally accepted that hyperammonemia plays a crucial role. Increased plasma ammonia levels are toxic for the brain, contribute to brain edema and stimulate inhibitory neurotransmission. A very essential liver function is detoxifying blood ammonia, primarily by urea synthesis and secondarily by glutamine synthesis. Urea is non toxic and is rapidly excreted by the kidneys. Glutamine is non-toxic as well and can be used as metabolic substrate by different organs among which the intestine. In addition, the cell source should display detoxification of other accumulating endogenous toxic compounds mainly through the cytochrome P450 system, synthesis of blood proteins and homeostasis of amino acids, lipids and carbohydrates.

Many liver cell types have been used for preclinical and clinical application of BAL devices. The choice for the optimal cell source for BAL, support devices is, however, still a matter of debate. Particularly, the availability, degree of liver specific function, and safety aspects are ongoing issues. Primary hepatocytes, either allogeneic or xenogeneic, have an excellent function and from that perspective would appear to be the favorite cell sources for BAL application.

However, mature porcine hepatocytes are not attractive, for clinical application because of the obvious risks and objections related to methods of treatment of human beings involving xenotransplantation.

Mature human hepatocytes, on the other hand, are scarce, as their sources are limited to either discarded donor livers or small parts obtained during liver resections.

Human hepatic cell lines have the advantage of an infinite proliferation capacity and can potentially serve as a stable cell source. In addition, the use of such cell lines from human origin would effectively avoid the xenotransplantation associated risks and objections. From these perspectives human hepatocyte cell lines seem to offer the most promising starting point for successful BAL development. Not surprisingly therefore, a lot of effort has been invested in finding and developing human hepatocyte cell lines having the required hepatic functionalities. So far, these efforts have only resulted in very limited success though.

The potential of a human fetal liver cell line cBAL111 for application in BAL systems has been tested and described by Poyck et al.[3]. Poyck et al. reported that cBAL111 eliminated ammonia at a rate up to 49% of that in primary porcine hepatocytes (PPH), despite a low urea production. Their synthetic functions (albumin production: 6%) and detoxification functions (lidocaine elimination: 1%) were to be low.

Uses of HepG2 cells or genetically modified variants thereof, in several BAL systems have been described by e.g. Nyberg et al.[4], Wang et al.[5], Enosawa et al.[6], and Takahashi et al.[7]. It is now well-established that the urea cycle is not maintained in HepG2 cells resulting in the lack of ammonia detoxification via this route. Gene expression data from HepG2 cells reveals limited expression of three urea cycle genes Carbamoyl Phosphate Synthase I (CPS), Arginosuccinate Synthetase (ASS) and Arginosuccinate Lyase, whereas no expression of Ornithine Transcarbamylase can be established.

According to Mavri-Damelin et al.[8], a HepG2 sub-clone, designated C3A, nevertheless had been found to produce urea. Their research confirmed that gene expression of ornithine transcarbamylase (OTC) and arginase I (Arg I), were completely absent. Arginase II (Arg II) mRNA and protein was expressed at high levels in C3A cells though and was inhibited by $N^{\omega}$-hydroxy-nor-L-arginine, which prevented urea production, thereby indicating a urea cycle-independent pathway. The authors conclude that the urea cycle is non-functional in C3A cells, and that these cells therefore cannot provide ammonia detoxification in a BAL system via urea. The authors note that this emphasizes the continued requirement for developing a component capable of a full repertoire of liver function, including an intact urea cycle to detoxify ammonia.

Kosuge et al.[9] reported that in gene expression profiles of bioreactor grown FLC-4, FLC-5 and FLC-7 cells some genes for liver functions were expressed at a level similar to that in normal liver, although none of the cell lines expressed the complete set of genes encoding ammonium metabolising enzymes or cytochrome P450 species. The use of a BAL system loaded with FLC-4 cells for treating pigs with hepatic dysfunction was reported by Kanai et al.[10]. However, the FL-4 cells were defect in their urea cycle.

Saito et al.[11] reported the development of a BAL system comprising FLC-5 cells. To assess hepatocyte function of the cells incubated in the BAL, expression of urea cycle and albumin synthesis enzymes were studied. The authors reported the presence of urea in the medium and an increase in the expression of urea cycle enzymes ASS and Arg I for the BAL incubated cells, whereas albumin synthesis had decreased. All in all, no FLC cell line has been obtained so far providing complete metabolic functionality that would render it suitable for clinical BAL application.

US 2005/0064594 discloses a liver cell line, designated HepaRG, which approximates human hepatocytes in cytochrome P450 3A activity (CYP3A4), which is a key factor in detoxification, after culturing for 14 days in HepaRG medium with 2% of dimethylsulfoxide (DMSO) after an initial 14-days proliferation phase without the addition of DMSO. In these cultures growth as well as many of the required hepatic functions other than CYP3A4, like urea synthesis and albumin synthesis are suppressed.

In summary, each of the human cell lines described above all have certain detoxification and/or metabolic liver functionalities, whereas certain other, essential, detoxification and/or metabolic liver functionalities are substantially reduced compared to those in freshly isolated human hepatocytes. In particular, until now, it has been problematic to acquire cells with a broad spectrum functionality, resembling that of freshly isolated human hepatocytes, to the extent that they are in fact suitable for successful clinical BAL application. Consequently, so far, it has proven impossible to develop a human cell line based BAL system providing complete hepatic functionality, especially a system providing both detoxification functionality as well as complete metabolic functionality.

It was the objective of the present inventors to provide adequate solutions to these short-comings of the prior art cells and BAL systems, thereby bringing successful clinical application a significant step closer.

SUMMARY OF THE INVENTION

The present inventors have managed to develop human hepatocyte cell line cultures that display broad-spectrum functionality, exceeding that of the cell lines currently known in the art. More in particular cell cultures are provided that display RNA expression profiles and hepatic functionality, inter alia, ammonia elimination, urea synthesis, ApoA1 production and albumin production, which render them suitable for effective clinical BAL application.

The present inventors have established that meeting this objective requires use of the proper cell line as well as using proper conditions for directing differentiation of the cells. More, in particular, it was found feasible to direct the differentiation of certain cell lines into the desired phenotype depending on the presence or absence of certain chemicals in the culture media.

The present inventors furthermore established that the functionality of the cell cultures is enhanced by culturing in a system allowing for three-dimensional growth, e.g. in a bioreactor comprising a three-dimensional solid support.

As will be explained here after in more detail, cell cultures can be obtained in accordance with the invention, having unparalleled broad-spectrum hepatic functionality.

Thus, the present invention provides cell cultures, a bioreactor containing them and BAL systems as well as their uses and their methods of manufacture. Furthermore, the present invention provides methods of improving the functionality of hepatic cell line derived cultures by culturing them in specific culture media and/or under conditions allowing for three-dimensional growth.

These and other aspects of the invention will be explained and illustrated in more detail in the following description and examples.

DETAILED DESCRIPTION OF THE INVENTION

Human Hepatocyte Cell Line Cultures

A first aspect of the invention concerns a cell culture comprising differentiated cells from a human hepatocyte cell line in a suitable culture medium, wherein said differentiated cells have constitutively liver-specific metabolic activity.

By "cell culture" or "culture", is normally meant an artificial in vitro system containing viable cells, whether quiescent, senescent or (actively) dividing. In a cell culture, cells are grown and maintained at an appropriate temperature, typically a temperature of 37° C. and under an atmosphere typically containing oxygen and $CO_2$. Culture conditions may vary widely for each cell type though, and variation of conditions for a particular cell type can result in different phenotypes being expressed. The most commonly varied factor in culture systems is the growth medium. Growth media can vary in concentration of nutrients, growth factors, and the presence of other components. The growth factors used to supplement media are often derived from animal blood, such as calf serum.

In accordance with a preferred embodiment of the present invention, the medium containing the differentiated cells can be any medium wherein viability and phenotype of the cells is maintained. This medium in which the differentiated cells are contained is not necessarily the same as the medium(s) employed for the proliferation and/or differentiation stages, which may require specific medium compositions as will be explained hereafter. Preferably said suitable medium containing the differentiated cells at least comprises serum, hormones, growth-factors and antibiotics. As will be understood by the person skilled in the art, serum free chemically defined media may be used instead without departing from the scope of the invention. For the reasons explained below, it is also preferred that said medium does not contain substantial amounts of DMSO, most preferably it is free from DMSO.

As will be known to the skilled person, cells can be provided in suspension or adherent cultures. Some cells naturally live in suspension, without being attached to a surface, such as cells that exist in the bloodstream. There are also cell lines that have been modified to be able to survive in suspension cultures so that they can be grown to a higher density than adherent conditions would allow. Adherent cells require a surface, such as plastic, which may be coated with extracellular matrix components to increase adhesion properties and provide other signals needed for growth and differentiation. Most cells derived from solid tissues are adherent. Another type of adherent culture involves growing cells in a three-dimensional environment as opposed to two-dimensional culture dishes. This 3D culture system is biochemically and physiologically more similar to in vivo tissue. Liver cells are typically polarized cells and function optimally when growing under cell-cell contact conditions in 3D configuration. Therefore, in accordance with the present invention, it is preferred that the cell culture comprises cells grown in a 3D culture, typically on a three-dimensional support matrix material, as will be explained in more detail hereafter.

Furthermore, the cell cultures of the present invention are typically in a state of confluence. The term "confluence" as used herein, refers to a density of cultured cells in which the cells contact one another covering most or all of the surfaces available for growth. During pre-confluent growth, selected cells behave like regenerating hepatocytes demonstrating corresponding patterns of regulation of gene expression. Upon reaching confluence, the cells assume an adult phenotype wherein cell division slows dramatically (typically doubling time >200 hr).

Human hepatocytes are the cells making up 70-80% of the total cell mass of the human liver. Hepatocytes are involved in protein synthesis, protein storage and transformation of carbohydrates, synthesis of cholesterol, bile salts and phospholipids, and detoxification, modification and excretion of exogenous and endogenous substances. Primary hepatocytes are typically separated from liver by collagenase digestion. This process creates a suspension of hepatocytes, which can be cultured and plated for immediate use, optionally cryopreserved. Primary mature human hepatocytes obtained in this way do not proliferate in culture. As mentioned above this effectively renders them unsuitable for use in BAL systems. The present invention therefore concerns hepatocyte cell lines.

The term "cell line", as used in the context of the present invention applies to cells cultured in vitro that have arisen from a primary culture and are capable of successful subculture. Primary cultures of differentiated mature mammalian cells do not multiply in culture or cease to multiply in culture after a limited number of divisions. The hepatocyte cell lines according to the present invention are typically capable of a significant number of cell divisions. Preferably, the present cultures contain cells obtained after at least 20, 30, 40, 50, 60, 70, 80, 90, and preferably at least 100 population doublings. This capability is typically found in cells derived from hepatic tumours but it can also be attained by immortalization of primary mature or fetal hepatocytes or in stem cells that might differentiate into hepatocytes. These stem cells may derive from a variety of sources including embryonic stem cell lines, liver, and other tissues, like pancreas, fat, bone marrow and cord-blood. The capability of the cells according to the invention to multiply indefinitely advantageously allows for the obtaining of large amounts of cells by multiplication or proliferation of these cells in vitro.

Thus, in a particularly preferred embodiment of the invention a cell culture is provided as defined herein before wherein said cells have a high proliferation capacity, but also have the capacity to retain or gain hepatic functionality.

A particularly preferred example of such a cell line is designated HepaRG as deposited on 5 Apr. 2001 at the Collection Nationale de Cultures de Microorganismes, Institut pasteur, under No. 1-2652. As stated before, this cell line has been described in the prior art, e.g. in US 2005/0064594. This document however teaches to employ a medium containing DMSO to initiate differentiation. The cell cultures thus obtained display mainly liver-specific detoxification functionality. The present inventors have for the first time produced a cell culture based on HepaRG cells differentiated under different conditions, yielding cell cultures displaying significant metabolic activity, but also synthetic and detoxification properties.

In another particularly preferred embodiment of the invention, a cell culture, is provided, comprising differentiated cells clonally derived from the aforementioned HepaRG cell line, including cells that have been derived from HepaRG using recombinant DNA techniques.

In other embodiments of the invention, cell lines designated HepG2 (ATCC number: HC-8065) and cBAL111 (Deurholt[19]) are used. The present inventors found that these cell lines can also suitably cultured in accordance with the methods of the present invention to yield cell cultures displaying significantly enhanced hepatic functionality as compared to cultures grown under conditions previously described, as will be illustrated in more detail in the examples. Cellular differentiation is the process by which a less specialized cell becomes a more specialized cell type. Differentiation occurs numerous times during the development of a multicellular organism as the organism changes from a single zygote to a complex system of tissues and cell types. Differentiation can dramatically change a cell's size, shape, membrane potential, metabolic activity, and responsiveness to signals. These changes are largely due to modifications in gene expression; with a few exceptions, cellular differentiation never involves a change in the genome itself. Each specialized cell type in an organism expresses a subset of all the genes that constitute the genome of that species. Cell differentiation thus involves a switch from one pattern of gene expression to another. In accordance with the present invention the term "differentiated cells" is thus used to indicate that the cells of the human hepatocyte cell line have been cultured under certain predetermined conditions in order for them to adopt a certain pattern of gene expression resulting in a specific phenotype. Differentially differentiated cells are physically distinct entities, as will be recognized by the skilled person. As noted before, in accordance with the invention, the cells have differentiated such as to display liver-specific activity, as will be explained in more detail here after.

In the normal functioning liver, the major metabolic functions of hepatocytes can be divided into three major categories: carbohydrate metabolism, fat metabolism and protein metabolism. Carbohydrate metabolism mainly involves maintenance of normal blood glucose levels. Hepatocytes house many metabolic pathways including glycogenesis, glycogenolyis and gluconeogenesis. Many aspects of lipid metabolism are carried out predominantly by the liver (although few are unique to the liver). Major examples of the role of the liver in fat metabolism include oxidation of triglycerides and synthesis of lipoproteins, cholesterol and phospholipids. The most critical aspects of protein metabolism that occur in the liver are deamination and transamination of amino acids, followed by conversion of the non-nitrogenous part of those molecules to glucose or lipids; removal of ammonia from the body by synthesis of urea; synthesis of non-essential amino acids; and synthesis of most of the plasma proteins. Albumin, the major plasma protein, is synthesized almost exclusively by the liver. Also, the liver synthesizes many of the clotting factors necessary for blood coagulation and produces growth factors. Hence, the term "liver metabolic functionality" as used in the context of the present invention, in principle encompasses any one or more of the above functions. However, as noted above, the present invention, in particular aims at improving the metabolic functionality of the cells with the purpose of treating subjects suffering liver failure. In this respect, as will be understood by the skilled person, some of the above liver metabolic functions are more critical than others.

In accordance with the invention, liver specific metabolic activity is preferably characterized, by a functioning urea cycle, preferably by a rate of ammonium elimination and/or urea production above a certain predetermined minimum, such as to render them suitable for practical BAL application.

Hence, in a preferred embodiment of the invention a cell culture as defined herein before is provided, characterized by a rate of ammonia elimination of at least 0.05 µmol/h/mg protein, under suitable culture conditions. More preferably said rate is at least 0.1 µmol/h/mg protein, most preferably at least 0.2 µmol/h/mg protein. Preferably, the rate of elimination of ammonia by a preferred cell culture of the invention is at least about 5, 10, 25, 50 or 75% of the rate of primary mature human hepatocytes under substantially identical in vitro culture conditions.

Furthermore, in a preferred embodiment of the invention a cell culture as defined herein before is provided, characterized by a rate of urea production of at least 0.003 µmol/h/mg protein, under suitable culture conditions. More preferably said rate is at least 0.005 µmol/h/mg protein, most preferably at least 0.010 µmol/h/mg protein. Preferably, the rate of urea production by a preferred cell culture of the invention is at least about 1, 2, 5, 10, 25, 50 or 75% of the rate of primary mature human hepatocytes under substantially identical in vitro culture conditions.

Urea may also be produced without elimination of ammonia. In a preferred embodiment of the invention a cell culture as defined herein before is provided, characterized by a % of urea derived from exogenously added ammonia of at least 10% of the total produced urea, under suitable culture conditions. More preferably said ratio urea formed from exogenously added ammonia versus total produced urea is at least 15%, most preferably at least 30%.

In addition to the urea cycle, liver specific metabolic activity in accordance with the present invention also preferably involves other protein, carbohydrate and/or lipid metabolic mechanisms.

In accordance with the present invention, the present cell cultures preferably are also characterised by their ability to produce albumin. Serum albumin is the most abundant blood plasma protein and is normally produced in the (healthy) liver. Serum albumin is important in regulating blood volume by maintaining the oncotic pressure (also known as colloid osmotic pressure) of the blood compartment and is an important transporter of many non-water soluble compounds like e.g free fatty acids and bilirubin. As will be shown in more detail in the examples, a cell culture is provided by the present inventors capable of producing albumin at a rate of about 10 ng/h/mg protein. Hence, in a preferred embodiment of the invention a cell culture as defined herein before is provided, characterized by a rate of albumin production of at least 1 ng/h/mg protein, under suitable culture conditions. More preferably said rate is at least 2 ng/h/mg protein, still more preferably at least 5 ng/h/mg protein and most preferably at least 10 ng/h/mg protein. Preferably, the rate of albumin production by a preferred cell culture of the invention is at least about 5, 10, 25, 50 or 75% of the rate of primary mature human hepatocytes under substantially identical in vitro culture conditions.

In accordance with the present invention, the present cell cultures preferably are also characterised by their ability to produce Apo A1. Apolipoprotein A1 is the major protein component of high density lipoprotein (HDL) in plasma and promotes cholesterol efflux from tissues to the liver for excretion. The protein is normally produced in the healthy liver and intestine. The capability of the present cell cultures to produce Apo A1 is therefore also typically indicative of adequate metabolic functionality. In addition, ApoA1 has an anti-inflammatory effect, which may be beneficial during liver disease. In a preferred embodiment of the invention a cell culture as defined herein before is provided, characterized by a rate of Apo A1 production of at least 0.002 ng/h/mg protein, preferably at least 0.005 ng/h/mg, more preferably at least 0.01 ng/h/mg, more preferably at least 0.02 ng/h/mg, especially at least 700, at least 1000, at least 1500 or at least 2000 ng/h/mg protein. Preferably, the rate of Apo A1 production by a preferred cell culture of the invention is at least about 5, 10, 25, 50 or 75% of the rate of primary mature human hepatocytes under substantially identical in vitro culture conditions.

Furthermore, adequate gluconeogenesis by the cells, in particular lactate consumption and glucose production rates are also considered indicative of liver metabolic functionality. Hence, in a preferred embodiment of the invention a cell culture as defined herein before is provided, characterized by a rate of lactate consumption of at least 0.02 µmol/h/mg protein, under suitable culture conditions. More preferably said rate is at least 0.05 µmol/h/mg protein, most preferably at least 0.1 µmol/h/mg protein. Preferably, the rate of lactate consumption by a cell culture of the invention is at least about 5, 10, 25, 50 or 75% of the rate of primary mature human hepatocytes under substantially identical in vitro culture conditions.

Furthermore, in a preferred embodiment, the cells display liver-specific detoxification activity, typically characterized by a rate of production of 6β-hydroxy-testosterone from testosterone of at least 0.5, preferably at least 1.0, more preferably at least 2.0 nmol/h/mg protein, under suitable culture conditions. Preferably, the 6β-hydroxy-testosterone production rate of the cell culture is at least about 20, 40, 60, 80, or 100% of the rate of primary mature human hepatocytes under substantially identical in vitro culture conditions. As will be understood by the skilled person, adequate detoxification functions of the cells are also characterized by the expression of certain genes, coding for the enzymes or proteins involved in these functionalities. In a particularly preferred embodiment, said differentiated cells having constitutively liver-specific metabolic activity are characterized by at least two, preferably three, more preferably all, of the following metabolic parameters:

a rate of ammonia elimination of at least 0.05 µmol/h/mg protein;

a rate of urea production of at least 0.003 µmol/h/mg protein;

a rate of apoA1 production of at least 15 ng/h/mg protein;

a rate of lactate consumption of at least 0.02 µmol/h/mg protein and a rate of albumin production of at least 1 ng/h/mg protein In another particularly preferred embodiment, said differentiated cells having constitutively liver-specific activity are characterized by at least three, preferably four, more preferably all, of the following parameters:

a rate of ammonia elimination of at least 0.05 µmol/h/mg protein;

a rate of urea production of at least 0.003 µmol/h/mg protein;

at least 10% urea produced from exogenously added ammonia of total produced urea a rate of apoA1 production of at least 700 ng/h/mg protein;

a rate of lactate consumption of at least 0.02 µmol/h/mg protein;

a rate of albumin production of at least 1 ng/h/mg protein and a rate of 6β-hydroxy-testosterone production of at least 0.5 nmol/h/mg protein As will be understood by the skilled person, adequate urea cycle functionality as well as other functions of the cells are also characterized by the expression of certain genes, coding for the enzymes or proteins involved in these functionalities. The expression of most genes is regulated at the transcription level. Therefore the expression levels of specific genes can be determined by reverse-transcriptase polymerase chain reaction (RT-PCR). As indicated by Hoekstra et al.[12], mRNA quantification can be carried out by normalization for the 18S rRNA starting level and subsequently standardized for average mRNA starting levels of two independent human healthy liver samples.

HNF4 (Hepatocyte Nuclear Factor 4) is a nuclear receptor protein mostly expressed in the liver. HNF4 has been found to be a central player in the hepatocyte nuclear factor network driving hepatic differentiation and function, driving e.g. the expression of proteins involved in detoxification and lipid metabolism and blood proteins, as well as other hepatocyte specific transcription factors. The present inventors believe that HNF4 expression is indicative of hepatic differentiation. As will be shown in more detail in the examples, a cell culture is provided by the present inventors having HNF4 transcript levels of up to about 250%. Hence in a preferred embodiment of the present invention a cell culture as defined herein before is provided, characterized by transcript levels of HNF4 of at least 50% of the in vivo level. More preferably, said transcript level is at least 100% and most preferably at least 200% of that of healthy adult liver.

The pregnane X receptor (PXR), also known as NR1I2 (nuclear receptor subfamily 1, group I, member 2), is a nuclear receptor that can up-regulate the expression of proteins involved in the detoxification and clearance of these substance from the body. One of the primary targets of PXR activation is the induction of CYP3A4, an important phase I oxidative enzyme that is responsible for the metabolism of many drugs. The present inventors believe that a significant rate of PXR expression is indicative of adequate liver-specific detoxification functionality. As will be shown in more detail in the examples, a cell culture is provided by the present inventors having PXR transcript levels of about 70%. Hence in a preferred embodiment of the present invention a cell culture as defined herein before is provided, characterized by transcript levels of PXR of at least 25% of the in vivo level. More preferably, said transcript level is at least 50% and most preferably at least 80% of that of healthy adult liver.

Carbamoyl phosphate synthetase (CPS) is the enzyme that catalyzes the reaction of ammonia and bicarbonate to produce carbamyl phosphate. Under normal physiological conditions CPS is the rate limiting enzyme of the urea cycle. During one turn of the urea cycle one nitrogen of urea is derived from ammonia and one from aspartate. The urea cycle is an essential liver specific function to protect the body (especially the brain) against hyperammonemia. Hence in a preferred embodiment of the present invention a cell culture as defined herein before is provided, characterized by transcript levels of carbamoyl phosphate synthetase (CPS) of at least 20% of the in vivo level. More preferably, said transcript level is at least 40, 50, 75 or 90% of that of healthy adult liver.

Ornithine transcarbamoylase (OTC) (also called ornithine carbamoyltransferase) is an enzyme that catalyzes the reaction between carbamoyl phosphate (CP) and ornithine (Orn) to form citrulline (Cit) and phosphate ($P_i$). OTC in mammals is located in the mitochondria and is part of the urea cycle. Hence in a preferred embodiment of the present invention a cell culture as defined herein before is provided, characterized by transcript levels of Ornithine transcarbamoylase (OTC) of at least 25% of the in vivo level. More preferably, said transcript level is at least 30, 35, 40 or 50% of that of healthy adult liver.

Arginase I (Arg I) is an enzyme that catalyzes the synthesis of urea from arginine. Arg I in mammals is located in the cytoplasm and is part of the urea cycle. In an embodiment of the present invention a cell culture as defined herein before is provided, characterized by transcript levels of Arginase I (Arg I) of at least 15% of the in vivo level. More preferably, said transcript level is at least 20, 35, 40 or 50% of that of healthy adult liver.

Glutamine synthetase (GS) is an enzyme that plays an essential role in the metabolism of nitrogen by catalyzing the condensation of glutamate and ammonia to form glutamine. As such, significant GS transcript levels are typically indicative of adequate liver metabolic functionality. As will be shown in more detail in the examples, a cell culture is provided by the present inventors having GS transcript levels of about 300%. Hence, in a preferred embodiment of the invention a cell culture as defined herein before is provided, characterized by transcript levels of glutamine synthetase (GS) of at least 100% of the in vivo level. More preferably, said transcript level is at least 200, 250 or 300% of that of healthy adult liver.

Cytochrome P450 3A4 (abbreviated CYP3A4), a member of the cytochrome P450 mixed-function oxidase system, is one of the most important enzymes involved in the metabolism of xenobiotics in the human body. CYP3A4 is involved in the oxidation of the largest range of substrates of all the CYPs. CYP3A4 is also, correspondingly, present in the largest quantity of all the CYPs in the human liver. The present inventors believe that a significant rate of CYP3A4 expression is indicative of adequate liver-specific detoxification functionality. Hence in a preferred embodiment of the present invention a cell culture as defined herein before is provided, characterized by transcript levels of CYP3A4 of at least 70% of that of the in vivo level. More preferably, said transcript level is at least 20, 40 or 100% of that of healthy adult liver.

In a particularly preferred embodiment, said differentiated cells having constitutively liver-specific metabolic activity are characterized by at least two, preferably three of the following metabolic parameters:
  a CPS expression level exceeding 20%, preferably exceeding 40%;
  a GS expression level exceeding 250%, preferably exceeding 300%; and
  an OTC expression level exceeding 25%, preferably exceeding 35%;

In another particularly preferred embodiment, said differentiated cells having constitutively liver-specific metabolic activity are characterized by at least four, more preferably all of the following parameters:
  a HNF4 expression level exceeding 250%, preferably exceeding 300%;
  a PXR expression level exceeding 70%, preferably exceeding 100%;
  a CPS expression level exceeding 20%, preferably exceeding 40%;
  an Arg I expression level exceeding 15%, preferably exceeding 35%;
  a GS expression level exceeding 250%, preferably exceeding 300%; and
  a CYP3A4 expression level exceeding 70%, preferably exceeding 100%;

As will be understood by the skilled person, each of the above recited parameters define a functional capacity of a differentiated hepatocyte cell line culture, i.e. an activity of which the differentiated cells of such culture are capable. It will be understood that whether or not such activity is actually taking place will depend on external factors such as the presence of the required substrates, ligands, targets, etc. in the culture medium. Hence, whenever reference is made herein above to 'suitable culture conditions', it will be clear to the skilled person that, in essence, standard culture conditions are referred to, i.e. conditions under which cells can be kept while maintaining their viability, with the additional requirement that such substrates, ligands, targets, etc. required for the respective activity are present in the medium within given standard concentration ranges. It is in any case within the skills of a trained professional to asses the capacity of a given human hepatocyte cell line culture to perform any of the aforementioned hepatic functions.

Method of Producing a Differentiated Hepatocyte Cell Culture

A second aspect of the present invention concerns a method of producing a cell culture comprising differentiated cells from a human hepatocyte cell line in a medium, wherein said differentiated cells have constitutively liver-specific activity.

Said method comprises selection of a suitable cell line. A suitable cell culture may have low hepatic functions when the cells are in expansion phase, however at confluence these cells typically display transcript levels of transcription regulators HNF4 and PXR, of at least 20% of the levels in vivo. More preferably, said transcript level is at least 30, 50 70% and most preferably at least 75% of that of adult liver.

As noted above, a particularly suitable cell line for the purpose of the present invention is the cell line designated HepaRG or a cell line that is clonally derived therefrom. Other cell lines that may suitably be used in accordance with this aspect of the invention include the cell lines designated HepG2 and cBAL111 or cell lines clonally derived therefrom.

The present method includes expansion or proliferation of cells. In preferred embodiment of the invention, cells are expanded by culturing, typically in monolayer or in suspension, preferably attached to a culture surface, in a suitable medium, preferably comprising serum, hormones, growth-factors and anti-biotics. More preferably the medium at least comprises serum, typically 2-10%, insulin, typically 2.5-10 µg/ml; cortico-steroid, typically 25-100 µM; penicillin and/or streptomycin, typically 0.5-2 U/ml; and glutamine, typically 1-5 mM. In a particularly preferred embodiment a medium is used comprising Williams' E medium with approximately 10% fetal bovine serum; approximately 5 µg/ml insulin, approximately 50 µM hydrocortisone, approximately 1 U/ml penicillin/streptomycin and approximately 2 mM glutamine. After a proliferation phase, typically at confluence, the cells can be induced to undergo differentiation. Alternatively, cells may be harvested and be used for further expansion.

In a preferred embodiment of the invention the cells are subsequently cultured under conditions suitable for inducing differentiation. For this purpose the cells are typically cultured in a suitable medium incorporating an effective amount of carbamoyl glutamate (CG). The present inventors found that the presence of CG induces or enhances urea production capacity in the cells of the invention. In addition, the urea production from exogenously added ammonia is typically significantly enhanced. It was found, unexpectedly, that treatment with CG has a preconditioning effect; when the cells are exposed to carbamoyl glutamate for at least 5 days, the increased urea production will be maintained for at least 24 hrs upon withdrawal of the CG. Typically, the, instantaneous effect of CG is negligible. The cell culture medium thus preferably comprises an amount of CG of at least 0.1, 0.2, or 0.5 mM, for example 1.0 mM. Furthermore, the culture medium may typically comprise serum, hormones, growth-factors and antibiotics. More preferably the medium at least comprises serum, typically 2-10%, insulin, typically 2.5-10 µg/ml; cortico-steroid, typically 25-100 µM; antibiotic, typically 0.5-2 U/ml; and glutamine, typically 1-5 mM. In a particularly preferred embodiment a medium is used comprising Williams' E medium with approximately 10% fetal bovine serum, approximately 5 µg/ml insulin, approximately 50 µM hydrocortisone hemisuccinate, approximately 1 U/ml penicillin/streptomycin and approximately 2 mM glutamine.

In a particularly preferred embodiment of the invention, the phase of cell differentiation comprises culturing the cells in a culture medium that is substantially or completely free of DMSO, i.e. it preferably contains less than 1%, 0.5%, 0.1%, 0.05%, 0.01% or 0.001% DMSO or it contains 0% DMSO.

Furthermore, it is preferred that the complete culture medium employed for the proliferation stage is also substantially or completely free of DMSO. The inventors found that presence of DMSO drastically reduced the cell number, as deduced from the total protein content and inhibited gene expression of synthetic and metabolic genes, as CPS and albumin and galactose elimination.

During culturing, the cells are kept at a desired, biologically or physiologically acceptable temperature, typically a temperature of approximately 37° C.

Preferably, during culturing, the cells are oxygenated using an oxygen-containing gas or gas mixture, such as pure oxygen, air, or a gas mixture containing oxygen, preferably 20-99% oxygen, typically about 40% oxygen, in admixture with another inert and/or physiologically acceptable gas such as nitrogen and carbon dioxide, typically approximately 5% carbon dioxide. Furthermore, it is preferred that the atmosphere under which the cells are cultures is humidified.

Hence, in a particularly preferred embodiment of the present invention, a process is provided comprising:
  selecting a human hepatocyte cell line
  a phase of cell proliferation comprising culturing the cells of said human hepatocyte cell line in a suitable culture medium, preferably comprising serum, hormones, growth-factors and antibiotics;
  a phase of cell differentiation comprising culturing the cells in a suitable culture medium comprising an effective amount of CG, said culture medium furthermore preferably comprising serum, hormones, growth-factors and antibiotics.

In a preferred embodiment of the invention the cells are grown in a three-dimensional (3D) culture, typically on a three-dimensional support matrix material, as will be explained in more detail hereafter. As indicated before, the present inventors have found that growing the cells in a 3D culture enhances the development of broad-spectrum hepatic functionality. In a preferred embodiment of the invention a process as defined in any of the foregoing is provided, wherein the cells are grown and/or differentiated in a 3D culture, preferably on a three-dimensional support matrix, e.g. in a bioreactor as described in more detail hereafter.

In a particularly preferred embodiment of the invention, a cell culture is provided, obtainable by the above described processes.

In yet another embodiment, the invention provides a method of improving the functionality of hepatic cell line derived cultures by culturing them in a culture medium containing CG and/or in the absence of DMSO and/or under conditions allowing for three-dimensional growth, in accordance with what has been described in the foregoing.

In still another embodiment of the invention, the use of CG for improving the functionality of hepatic cell line derived cultures is provided, in accordance with what has been described in the foregoing.

Bioreactor

In a further aspect, the invention relates to a bioreactor comprising a cell culture of the invention or obtained in a method of the invention as described herein. The bioreactor of the invention may in principle be any suitable device for culturing and/or maintaining cells.

As stated in the introductory part of this application, many bioreactor configurations have been proposed and described. In this regard reference is made to Park and Lee[1] and Sgroi et al.[2], the entire contents of which are incorporated herein by reference, in particular the subject-matter described therein, relating to bioreactor configurations.

As will be understood by the skilled person, a bioreactor will typically comprise a vessel or chamber, comprising a wall defining and enclosing a three-dimensional space, said vessel or chamber being suitable for holding solid and/or liquid content, e.g. a cell culture and a culture medium. In accordance with the present invention the chamber or vessel is typically a closed system which does not allow for the exchange of matter between the space within the walls and the atmosphere surrounding said chamber or vessel. The wall of the reactor is thus typically be made of any suitable inert and liquid and gas impervious material, such as glass, plastic, e.g. plexiglass, polycarbonate or polysulfone, or metal. From a practical viewpoint a material selected from the group of polysulfone is preferred, these materials being able to withstand (steam) sterilization conditions. The inside of the reactor vessel can be provided with a special coating compatible with the cells to be cultured, such as collagen or Matrigel.

The size of the reactor is not particularly limited and will usually depend upon the capacity required. The volume of the reactor can therefore typically vary from 1 ml to 1000 liters. With a view to the intended incorporation of the bioreactor in a functional BAL system, as described herein below, suitable reactor volumes are within the range of 0.2-3 liter, most preferably within the range of 0.5-1 liter.

Typically, the bioreactor comprises a support matrix for attachment of the cells. The support matrix may e.g. comprise a three-dimensional solid support which may be in the form of a highly porous sheet or mat. Preferably such a three dimensional matrix comprises a physiologically acceptable network of fibers or a physiologically acceptable open-pore foam structure. Alternatively, the support matrix may be a semi-solid material, such as a gel. Suitable examples of matrix materials include Gelfoam, PVF (Collagen coated Reticulated Polyvinyl formal resin), PVLA-RPU (Poly-N-para-vinylbenzyl-lactonamide coated reticulated polyurethane) PGA (Polyglycolic acid), PVA (Polyvinylalcohol), PGA/PLA (polyglycolic acid/polylactic acid), 3D-Polyurethane foam or non-woven matrix, and Porous siliconrubber foam. In a particularly preferred embodiment the support matrix has the form of rolled up or folded sheets or mats. Although the solid support of the invention generally does not require a pre-treatment step before use, it is comprised within the scope of the invention to treat the support matrix with extracellular matrix materials, such as Matrigel, poly-N-paravinylbenzyl-lactonamide, collagen based materials, or with gaseous compounds, in a manner known per se, in order to further improve cell adhesion.

In a preferred embodiment of the invention the bioreactor comprises means for supplying gaseous oxygen and for removal of gaseous carbon dioxide. Such means may e.g. be in the form of conduits that are permeable to gasses like oxygen and carbon dioxide. Preferably the conduits are evenly distributed throughout the three dimensional matrix and more preferably the distance between individual conduits is between 0.05 mm and 5 mm. Suitable conduits are e.g. hollow fibers or capillaries made of a hydrophobic material and having an outer diameter of 0.1 mm to 1.0 mm. Preferably the bioreactor is provided with at least one gas inlet and at least one gas outlet operably connected to said capillaries.

Furthermore, it is preferred that the bioreactor of the invention comprises means for perfusing the matrix with a liquid medium; typically it comprises at least one liquid inlet and one outlet, operably connected to the space containing the cells of the invention, through which a liquid medium can be fed to this space and be brought into contact with the cells and respectively be removed there from. These liquid in- and outlets may thus be used for perfusing a liquid medium through the bioreactor whereby the cells of the invention in the bioreactor preferably produce, bioconvert or remove a substance in or from the medium.

Thus, typically, any bioreactor in accordance with this invention will at least comprise a chamber or vessel holding a matrix loaded with a cell culture as described herein before, said bioreactor further comprising means for oxygenating said matrix.

The reactor can further comprise all known elements of biological reactors, such as gas and/or liquid pumps operably connected to the different inlets or outlets; means for measuring and/or controlling the temperature within the reactor vessel; access means, such as a hatch, for accessing the inside of the reactor; inspection means; means for seeding cells, such as additional inlets, means for intervening sampling of cells, probes and means for inserting them, such as probes for the measurements of the viability as further described herein below, etc. The reactor may further be provided with means for the automatic control of the different reactor functions, such as a computer means operably connected with the pumps, temperature controlling means etc.

The reactor may also be provided with means for agitating the reactor, such as an electric motor, for instance for rotating the reactor along one of its axes, or with means for stirring inside the reactor, although the latter is usually not preferred.

Method of Producing a Differentiated Hepatocyte Cell Culture in a Bioreactor

A further aspect of the invention concerns the preparation of a bioreactor comprising a differentiated hepatocyte cell culture.

In accordance with the invention, the cells are first expanded at large scale outside the bioreactor. This may be carried out by culturing the cells in suspension or, preferably, attached to a culture surface, which may be provided by e.g. roller bottles, multilayer culture plates or using carriers in suspension in stirred or continuous-flow bioreactors under optimal oxygenation conditions. For harvesting, the cells will be exposed to a cell detachment solution of proteolytic and collagenolytic and DNAse enzymes. Preferably the cells are harvested with a 4:1 mixture of Accutase™ and Accumax™ (Innovative Cell Technologies, Inc., San Diego, USA).

The cells are introduced into a bioreactor as described herein before, after which they are allowed to attach and/or adhere to the support matrix during a suitable period of time. In cultivating the cells, the reactor can be loaded with a small amount of cells, after which the cells are allowed to divide so as to fully populate the reactor. According to this embodiment, the support matrix will only require loading of amounts of as low as 5% of the total cell capacity, so as to fully populate the reactor by advantageous "three dimensional" growth. Preferably, the reactor is loaded with an amount of 10-80%, more preferably 40-80%, more preferably 50-80%, most preferably 60-80%, of the total cell capacity. It is also possible to feed more cells into the reactor, so as to fully saturate the matrix material with adherent cells, or even to use an excess amount of cells, after which superfluous cells are removed. In general, the BAL will be seeded with $10^5$-$10^9$ cells/ml, usually around 10-500 *$10^6$ cells/ml and/or with an amount of cells corresponding to at least 5%, 10%, 15% or 20% of normal liver mass. The reactor is usually seeded by injecting a suspension of the cells into the reactor, after which the cells are allowed to distribute themselves throughout the reactor and adhere themselves to the solid support during a suitable period of time. In order to facilitate the distribution of the cell suspension even further, the reactor can be agitated after the cell suspension has been injected. According to a highly preferred embodiment, after injection of the cell suspension, the reactor is rotated, preventing the formation of a cell pellet at the bottom in the bioreactor, typically for 2-4 hours. After immobilisation of the cells is complete, the remaining suspension containing non-adhered and/or excess cells is removed from the reactor, by flushing the reactor with a suitable liquid medium.

After loading of the cells and adhering of cells to the matrix, the bioreactor is perfused with culture medium as described herein before, typically at a rate of 50-250 mL/min., e.g. at 150 mL/min, typically such as to allow them to undergo one or several population doublings. Furthermore, this process typically allows for the cells to reorganize in 3D, a process which typically enhances the hepatic functionality of the cells eventually obtained, as indicated herein before. The process is preferably continued until the cell culture in the bioreactor stops proliferating. This can be calculated from the loading mass as deduced from cell number, total protein or DNA content and previously determined population doubling time of the cell line in a bioreactor. It can also be deduced from the stabilization of oxygen consumption.

Subsequently, the reactor is perfused with culture medium to induce differentiation. During the differentiation phase, culturing hepatocyte cell lines, in particular the HepaRG cell line, in the bioreactor can upregulate their hepatic functions to an unexpectedly high degree. The inventors found a significant improvement of urea production and ammonia elimination and conversion of lactate production into lactate consumption and a significant increase of expression levels of CYP2B6 and CYP3A4 when HepaRG cells were cultured in a bioreactor under the conditions as described herein. Hence, in a particularly preferred embodiment of the invention, a method of producing a bioreactor is provided, comprising:
a phase of cell proliferation comprising culturing cells of a human hepatocyte cell line in a suitable culture medium, preferably comprising serum, hormones, growth-factors and antibiotics;
loading of viable cells to an amount of at least 5% of normal liver mass in a bioreactor comprising a support matrix, and allowing the cells to attach to said matrix;
an expansion or proliferation phase comprising culturing the cells in a suitable culture medium, preferably comprising serum, hormones, growth-factors and antibiotics, to achieve at least one population doubling; and
a differentiation phase comprising culturing the cells in a culture medium comprising serum, hormones, growth-factors and antibiotics.

In a preferred embodiment of the invention, during the differentiation phase, said culture medium comprises a suitable amount of CG, e.g. an amount of at least 0.5 mM, such as to further enhance urea production capacity of the cells, as explained herein before. In a particularly preferred embodiment of the invention, the culture media employed in said proliferation and differentiation phases are substantially or completely free of DMSO, as explained herein before.

The differentiation phase typically includes at least 7 days, more preferably at least 14, 21 or 28 days and up to 50 days.

Hence, in a particularly preferred embodiment of the invention, a method of producing a differentiated hepatocyte cell culture in a bioreactor is provided, comprising:
selecting a human hepatocyte cell line
a phase of cell proliferation comprising culturing cells of a human hepatocyte cell line in monolayer or in suspension, preferably attached to a culture surface, in a suitable culture medium, preferably comprising serum, hormones, growth-factors and antibiotics;
loading of viable cells to an amount of at least 5%, preferably 40-80%, of normal liver mass in a bioreactor comprising a support matrix, and allowing the cells to attach to said matrix;
a potential expansion or proliferation phase and reorganization in 3D phase comprising culturing the cells in a suitable culture medium, preferably comprising serum, hormones, growth-factors and antibiotics; and
a differentiation phase of at least 7 days comprising culturing the cells in a culture medium comprising an effective amount of CG, said medium further preferably comprising serum, hormones, growth-factors and antibiotics.

During culturing, the cells are kept at a desired, biologically or physiologically acceptable temperature, typically a temperature of approximately 37° C., e.g. by keeping the reactor in a thermostat, or by controlling the temperature of liquid and/or gas flows, as will be clear to one skilled in the art. The gas and liquid are preferably lead through the bioreactor continuously at suitable flow rates, using the afore mentioned liquid and gas in- and outlets of the reactor.

BAL System

A further aspect of the invention concerns a BAL system comprising a bioreactor as described herein before. The advantageous properties of the cells and the bioreactor of the invention make them especially suited for use in or as a bio-artificial liver system.

Therefore, in general, the bio-artificial liver system of the invention comprises a bioreactor of the invention comprising a support matrix loaded with a cell culture as defined hereinabove.

During use of the present BAL system, the bioreactor liquid medium in- and outlets are operably connected to the blood circulation of a subject by means of a liquid circuit, so that a liquid medium directly or indirectly derived from the subject is used to perfuse the bioreactor, allowing said cells to carry out functions normally carried out by the liver in vivo. Liquid medium leaving the bioreactor is returned to the subject directly or indirectly. The BAL-system of the invention will therefore comprise a liquid circuit for circulating the liquid medium, as well as one or more pumps for controlling the liquid flow through said circuit.

The circuit can also contain further appliances for the (pre-) treatment of the liquid medium, i.e. blood or plasma, such as an activated charcoal column for the absorption of hydrophilic toxins and/or a resin column for adsorption of hydrophobic substances (e.g. bilirubine). Other types of such detoxification systems or columns known to the skilled person may be included in the system as well or instead, without departing from the scope of the invention.

The liquid circuit may also comprise means for adding nutrients and other desired substances to the liquid medium, although in this respect the liquid medium derived from the patient may itself be sufficient for keeping the liver cells in the reactor viable. The same applies with regard to oxygen requirements of the cells; separate supply of oxygen does not need to be provided during perfusion of the bioreactor with an oxygen containing medium, such as blood. Preferably however the system does include a source of oxygen or oxygen containing gas. Such an oxygenation system is operably connected to a bioreactor gas inlet and a system for removing gas is operably connected to the bioreactor gas outlet. As will be understood by the skilled person, a pump may be connected to any gas conduit connected to the bioreactor gas in- and outlets.

During use, the Bioreactor of the invention can be perfused with whole blood—either arterial or venous—derived from a subject in a manner known per se, but preferably the bioreactor is perfused with plasma obtained from the blood. In this preferred embodiment, the BAL-system's liquid circuit will usually comprise a plasma separator or plasmapheresis unit for separating the plasma from the whole blood derived from the subject. The use of BAL-systems on the basis of plasmapheresis, as well as suitable plasmapheresis units, are well known in the field and are for instance described in V. d. Kerkhove et al[13], which is to be considered incorporated herein by reference.

The liquid circuit will also typically contain one or more cell filtering units, such as membrane filters, columns or hollow fibre modules with a suitable molecular weight cut off, either placed before or after the reactor. Since the present invention may employ tumorigenic cells, it is particularly preferred that one or more filtering units are incorporated in the circuit, placed downstream of the bioreactor, i.e. at the bioreactor liquid outlet side, with a view to reducing tumorigenicity associated risks for the subject to be treated.

Although dependant upon the geometry and capacity, the amount and activity of the cells present in the reactor, the desired therapeutic application and other such factors, the BAL-system of the invention is typically suitable for treating 1 to 300 ml of liquid medium derived from a patient per minute. In order to achieve this, the liquid medium can be fed directly to the reactor at a corresponding rate, e.g. of 50 mL/min. Preferably, the bioreactor of the invention is incorporated into a "high flow loop", as known per se from the abovementioned prior art. In such a loop, the flow of the liquid medium over the reactor can be kept at a higher or lower rate than the flow of liquid from the patient thereby providing for recirculation of the liquid medium over the reactor. Usually, this will be carried out by suitable control of the different pumps in such a high flow loop system, by keeping them at a suitable flow ratio.

The BAL system preferably comprises a single bioreactor as defined above comprising a cell culture in accordance with the invention. However, a BAL system may comprise a bioreactor connected in series and/or in parallel with one of more other bioreactors, typically containing distinct cell cultures or an artificial detoxification system. Hence, a Bioartificial liver device is also provided comprising a bioreactor as defined above comprising a cell culture in accordance with the invention in combination with another bioreactor comprising a chamber or vessel holding a matrix loaded with a cell culture containing differentiated cells of a human cell line, and furthermore comprising means for oxygenating said matrix, wherein the cells at least differ in their phenotype compared to the first bioreactor. Alternatively, the bioreactor as defined above comprising a cell culture in accordance with the invention is combined with an artificial detoxification module, e.g. a charcoal column or an albumin dialysis system.

In accordance with the present invention, it is preferred to combine in one BAL system modules providing distinct functionalities if a single bioreactor does not fully cover the functional spectrum or is to susceptible to detrimental effects of liver failure plasma or blood of the treated subject. More specifically, an artificial detoxification module or one or more further bioreactors may be combined with the liver-specific bioreactor of the present invention, said further bioreactors providing e.g. supplementary liver-specific detoxification functionality and/or immunologic functionality. Such a composite BAL comprises at least two consecutive bioreactors with cells differentiated into diverging directions: the first with detoxification phenotype preceding the second liver-specific bioreactor of the present invention. Alternatively, the composite BAL comprises an artificial detoxification module preceding the liver-specific bioreactor of the present invention. The plasma of the patient will be perfused through the detoxification bioreactor or module, to specifically eliminate and inactivate compounds toxic to the patient, which may also be toxic to the cells loaded in the bioreactor of the present invention. Subsequently the plasma will be perfused through the in bioreactor of the present invention which will execute most liver-specific functions, like ammonia elimination, urea production and synthesis of plasma proteins etc. A bioreactor with immunomodulatory characteristics can optionally be included after the bioreactor of the present invention.

The different elements of the BAL-circuit may be provided as an integrated system in a single housing, or the BAL may consist of separate connected elements.

Figure 1:
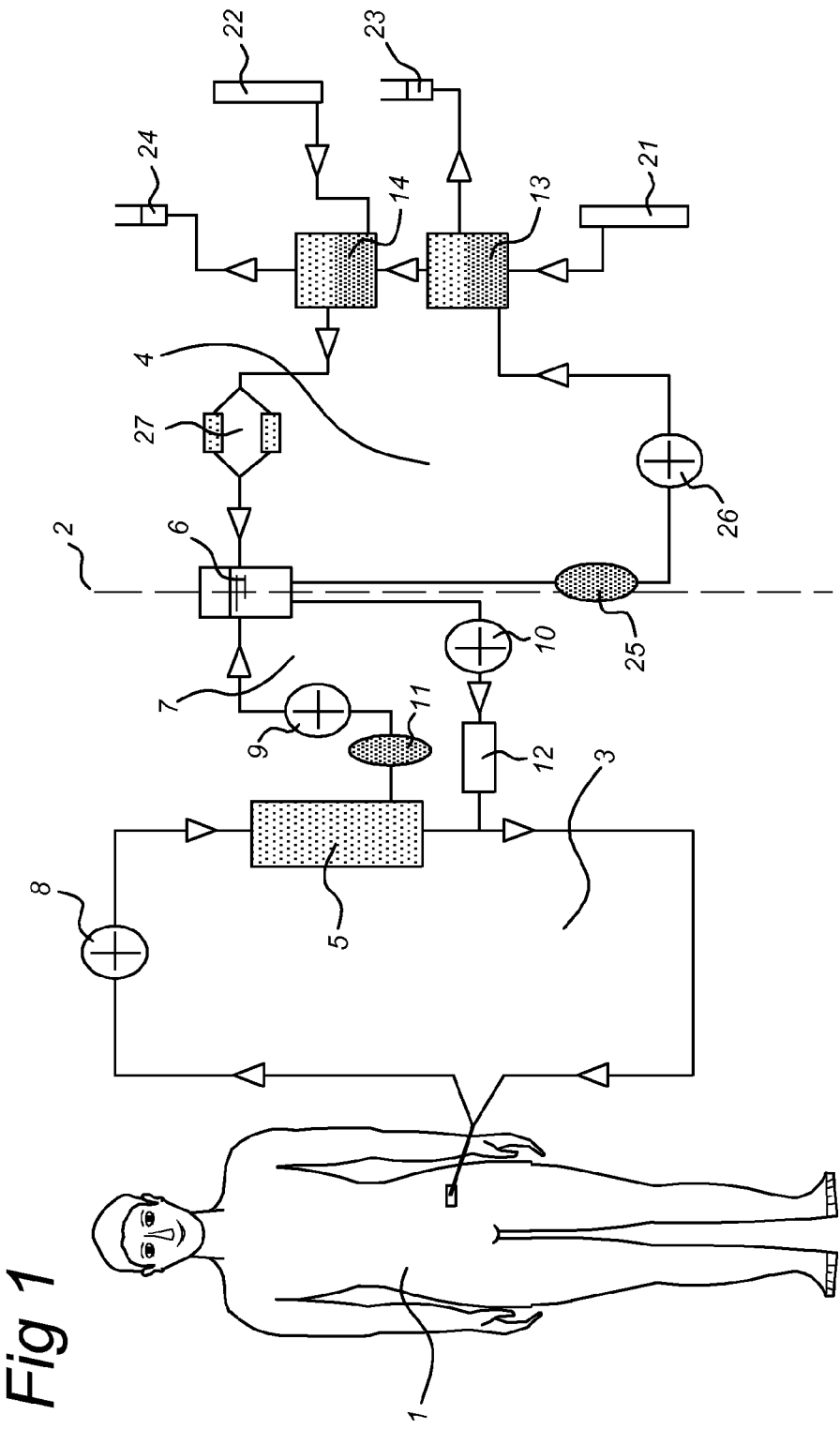
FIG. 1 schematically illustrates a high flow loop two-reactor bioartificial liver system including a plasmaphoresis unit according to an embodiment of the invention.

A possible configuration of a particularly preferred high flow loop two-reactor BAL system comprising a plasmapheresis unit is shown schematically in FIG. 1. Said figure shows a subject (1) to be treated, connected to the BAL system (2), which comprises a blood circuit (3) and a plasma circuit (4). The blood circuit comprises a plasmapheresis system (5), that separates plasma from the subject's blood, which plasma is lead to a plasma reservoir (6). Blood flowing out of the plasmapheresis system is combined with plasma coming from the plasma reservoir (6) and lead back to the subject. The blood circuit furthermore comprises a pump (8), set to produce a flow of blood of e.g. approximately 50 ml/min. Additional pumps (9, 10), a heater (11) and a filter (12) are incorporated in the plasmapheresis system—plasma reservoir loop (7). The plasma circuit comprises a detoxification bioreactor (13) and a metabolic bioreactor (14) connected in series. The plasma reservoir (6) is operably connected to the detoxification bioreactor; the detoxification reactor is operably connected to the metabolic bioreactor; and the metabolic bioreactor is operably connected to the plasma reservoir. Each reactor comprises a gas inlet operably connected to a source of a gas, such as a gas cylinder (21, 22) and a gas outlet system (23, 24). The bioreactor loop furthermore includes a heater (25), a pump (26), set to produce a flow of plasma of e.g. approximately 150 ml/min., and a filter (27).

Figure 2:
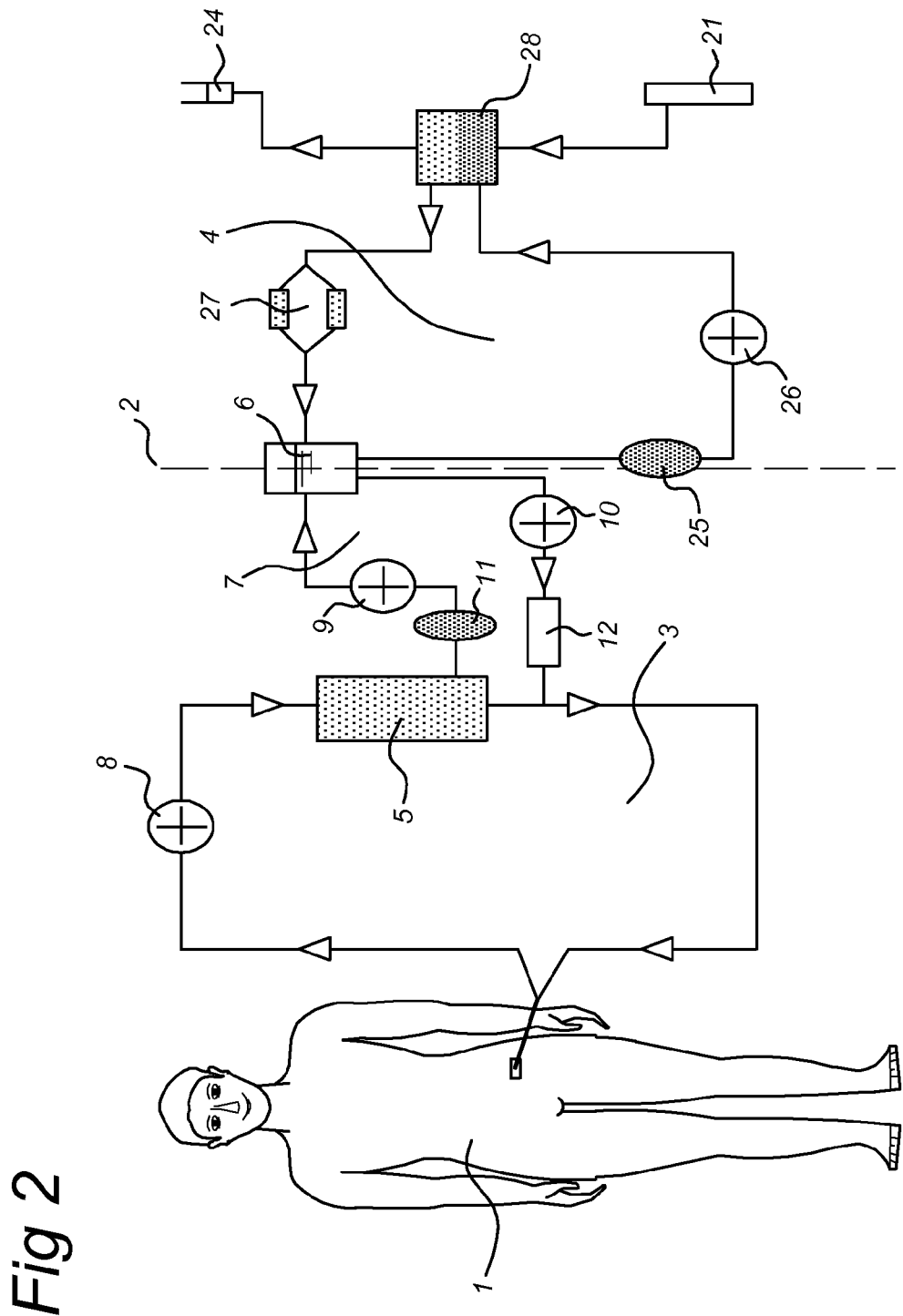
FIG. 2 schematically illustrates a one-reactor bioartificial liver system including a plasmaphoresis unit according to an embodiment of the invention.

A possible configuration of a particularly preferred one-reactor BAL system comprising a plasmapheresis unit is shown schematically in FIG. 2. Said figure shows a subject (1) to be treated, connected to the BAL system (2), which comprises a blood circuit (3) and a plasma circuit (4). The blood circuit comprises a plasmapheresis system (5), that separates plasma from the subject's blood, which plasma is lead to a plasma reservoir (6). Blood flowing out of the plasmapheresis system is combined with plasma coming from the plasma reservoir (6) and lead back to the subject. The blood circuit furthermore comprises a pump (8), set to produce a flow of blood of e.g. approximately 50 ml/min. Additional pumps (9, 10), a heater (11) and a filter (12) are incorporated in the plasmapheresis system—plasma reservoir loop (7). The plasma reservoir (6) is operably connected to the bioreactor (28) via the plasma circuit. The bioreactor comprises a gas inlet operably connected to a source of a gas, such as a gas cylinder (21) and a gas outlet system (24). The bioreactor loop furthermore includes a heater (25), a pump (26), set to produce a specific flow of plasma and a filter (27).

Treatment of Hepatic Failure

The cell cultures of the invention as well as the bioreactors and bioartificial liver systems containing them can be used to support and/or replace liver function in subjects with impaired liver function or in other cases in which artificial liver support is desirable and/or required. Hence further aspects of the invention concerns use of the cell cultures, bioreactors and/or BAL systems as described herein before for treating a subject in need of such treatment, typically for temporarily replacing and/or supporting hepatic functions in a subject in need thereof, as well as methods of treatment of such subjects, said method comprising extra-corporeal or 'liver support' employing said cell cultures, bioreactors and/or BAL-systems of the invention.

Typically, these aspects of the invention concern treatment of subjects suffering from acute liver failure, end stage liver disease or acute-on-chronic liver disease. Examples of these conditions may include fulminant hepatic failure (FHF), for instance due to viral hepatitis infections or acute liver poisoning (for instance with acetaminophen, CCl4, alcohol or drugs), as well as transient liver ischaemia, and liver trauma due to injury. It may also concern treatment to improve the subjects condition before liver transplant, to bridge the period before liver transplant, to bridge the rejection period after acute rejection of a transplanted liver, during the anhepatic phase while a liver transplant is carried out and/or during recovery of a liver transplant, or to allow time to regenerate the patient's own liver. Furthermore, it may concern treatment of subjects suffering from chronic liver diseases to enhance the quality of life of the patient and/or to bridge periods of exacerbation.

Treatment of the subject will typically involve perfusing the cell cultures contained in the BAL-system bioreactors with the subject's blood or plasma. Preferably this is done continuously for a period of time sufficient to stabilise and preferably improve haemodynamic and biochemical parameters, typically meaning that an amount of cells within the range of 5%, 10%, 20% or 30% of liver mass is perfused with the subjects plasma for 8-24 hours at a flow rate of 20-70 mL/min.

Before or during use, the functional effect and the metabolic performance of the bioreactor and the cells contained therein can be monitored in a manner known per se with any of the large number of tests available for this purpose, such as measurement of protein synthesis, ureagenesis, oxygen uptake (for which advantageously direct measurement at the gas inlet and gas outlet can be used), cytochrome P450-activity, drug metabolic assays, clearance techniques etc, see for instance Rozga et al.[14], incorporated herein by reference. Also, a biomass meter can be used, which uses conductivity measurements based upon differences in membrane potential between dead cells and living cells. Such a meter is known to one skilled in the art.

An advantageous aspect of the present invention resides in the preconditioning of the cell cultures using CG during culturing of the cells, such that the cells need not be exposed to (additional) CG during treatment of the patient in order to retain sufficient hepatic functionality for a suitable period of time. Hence in a preferred embodiment of the invention a method of treatment of a subject is provided, as defined herein before, wherein no external source of CG is added to the cell cultures during use of the bioreactor.

The different aspects of the invention as described here above will be illustrated by means of the following non-limiting examples.

EXAMPLE 1

Preparation of HepaRG Cell Cultures in Monolayer

HepaRG Culture in Monolayer

HepaRG cells are primarily expanded in monolayer at 37° C. in a humidified atmosphere (95% air, 5% $CO_2$), since proliferation reduces when the cells are cultured in the bioreactor. The culture medium (HepaRG medium) consists out of Williams' E medium (Lonza) with 10% fetal bovine serum (FBS, Lonza), 5 μg/ml insulin (Sigma), 50 μM hydrocortisone hemisuccinate (Sigma), 1 U/ml penicillin/streptomycin (Lonza) and 2 mM glutamine (Lonza). The applied FBS batch should be tested before large expansion of the cells will be carried out (see below).

Testing FBS Batch and Functionality in Monolayer

The performance of the HepaRG cells can be tested in monolayer to optimize culture conditions that may be applicable to BAL cultures as well. Furthermore the appropriate FBS batch can be selected, this way. Differences in functionality of the cells were found, depending on the batch of FBS used. Therefore the batch should be tested thoroughly before large scale culturing in Hyperflasks™ (Corning) and the bioreactor will be pursued.

For testing, the cells are seeded in 6-well and 24-well culture plates (Corning) in HepaRG media with different FBS batches or other differences in medium composition. After a 2 weeks proliferation phase, 2% of DMSO will be added to half of the cultures. After another 2 weeks of culturing, the confluence and morphology of the cultures will be assessed microscopically. Furthermore the +DMSO and −DMSO cell cultures in the 24-well plates will be tested for biochemical activity, i.e. urea production, ammonia elimination and protein content. The cultured cells are washed twice using phosphate buffered saline (PBS, NBPI International) and then incubated with test medium consisting of HepaRG culture medium supplemented with 1.5 mM $^{15}NH_4Cl$ (Sigma), 2.75 mM D-galactose (Sigma), 2 mM ornithine hydrochloride (Sigma) and 2 mM L-lactate (Sigma). Medium samples are taken after 1 hr from the culture wells, as a reference, and after 24 hours. At the end of the test period the cells are washed three times using PBS and stored at −20° C. for protein determination. From the changes in concentration at t=1 hr and 24 hr of urea and ammonia an activity per hour and per mg protein/well is calculated. Quality of the cell-loaded bioreactors, measured by hepatocyte function at the start of the treatment, will be compared with values of primary hepatocytes that have been tested extensively in vitro in the past.

The HepaRG cells cultured in the 6-well plates are lysed and the RNA is isolated using the RNeasy kit (Qiagen). Next, real-time reverse transcriptase-polymerase chain reactions (RT-PCR) are performed to quantify mRNA levels of hepatic genes as well as 18S ribosomal RNA levels by RT-PCR.

Biochemical Analysis

Ammonia: Ammonia concentrations are determined by an enzymatic kinetic colorimetric assay using glutamate dehydrogenase and NADPH, using the Ammonia (rapid) kit (Megazyme, Ireland) according to the instructions of the manufacturer.

Testosterone: Testosterone concentrations are determined high performance liquid chromatography coupled to mass spectrometry.

Urea: Urea concentrations of test medium samples are determined using the blood urea nitrogen test of Sigma Chemical Co according to the instructions of the manufacturer.

$^{15}$N Urea: Single and Double labelled urea is measured in the test medium samples using mass-spectrometry.

Albumin: Human albumin concentrations are determined by ELISA using goat-anti-human serum albumin antibody (1:100, Abcam, ab8940;) and HRP conjugated rabbit-anti-human serum albumin (1:5000, Abcam, ab7394).

ApoA1: Human ApoA1 concentrations are determined by ELISA using rabbit anti-human ApoA1 (1:500, Calbiochem, 178422), as first antibody, monoclonal mouse anti human ApoA1 (1:500, Calbiochem, 178472) as second antibody and polyclonal rabbit anti mouse IgG-HRP (1:2000, Dako Po 260) as third antibody.

AST and LDH: Both AST and LDH activities are analyzed spectrophotometrically using a P800 Roche Diagnostics analyzer.

Lactate and glucose concentration: Both are analyzed using a P800 analyzer (Roche Diagnostics).

Total protein: Total protein was quantified by spectrometry using Coomassie blue (Bio-Rad).

RT-PCR

First-strand cDNA is generated using a combination of 40 pmol of gene-specific RT-primers (see Table 1) and 134 units of Superscript III (Invitrogen) and 1 μg RNA in a total volume of 25 μl at 50° C. for one hour followed by a 15 min incubation at 70° C. The resulting gene-specific RT reaction mixtures are column purified using Qiaquick PCR Purification Kit (Qiagen).

Real-time PCR is performed using 1 μl of cDNA and LightCycler FastStart DNA Master SYBR® Green 1 reagent (Roche). PCR primers are depicted in the Table 3. The thermal cycling profile of the touchdown PCR is as follows: 94° C. for 10 min, followed by 40 cycles of 94° C. for 1 s, primer annealing at 68° C. for 7 s with a 0.5° C./cycle decrease until 63° C., and extension for 40 s at 72° C. PCR specificity is verified by melting curve analysis and agarose gel electrophoresis. The mRNA quantification is carried out by using the LinRegPCR programme (Ramakers et al.[17]). For each sample the mRNA starting level is normalised for the 18S rRNA starting level. To correct for variations between RT-PCR runs, the mRNA starting levels of liver specific genes of NKNT-3 cells are additionally standardized for average mRNA starting levels of two liver samples that are simultaneously subjected to RT-PCR.

TABLE 1

Primer sequences

| Gene | | primer 5'-3' | |
|---|---|---|---|
| 18S rRNA | RT | GCATCGCCGGTCGGCATCG | (SEQ ID NO: 1) |
| | S | TTCGGAACTGAGGCCATGAT | (SEQ ID NO: 2) |
| | AS | CGAACCTCCGACTTTCGTTCT | (SEQ ID NO: 3) |
| AAT | RT | GGGGGATAGACATGGGTATGG | (SEQ ID NO: 4) |
| | S | ACAGAAGGTCTGCCAGCTTC | (SEQ ID NO: 5) |
| | AS | GATGGTCAGCACAGCCTTAT | (SEQ ID NO: 6) |
| AFP | RT | CGTTTTGTCTTCTCTTCCCC | (SEQ ID NO: 7) |
| | S | TKCCAACAGGAGGCYATGC | (SEQ ID NO: 8) |
| | AS | CCCAAAGCAKCACGAGTTTT | (SEQ ID NO: 9) |
| ALB | RT | ACTTCCAGAGCTGAAAAGCATGGTC | (SEQ ID NO: 10) |
| | S | TGAGCAGCTTGGAGAGTACA | (SEQ ID NO: 11) |
| | AS | GTTCAGGACCACGGATAGAT | (SEQ ID NO: 12) |
| Arg I | RT | TGTGATTACCCTCCCGAGCAAGTC | (SEQ ID NO: 13) |
| | S | TTGGCAAGGTGATGGAAGAAACA | (SEQ ID NO: 14) |
| | AS | CCTCCCGAGCAAGTCCGAAACAA | (SEQ ID NO: 15) |
| Arg II | RT | ACAAGGGCAGAAAAGAAAAGGAGT | (SEQ ID NO: 16) |
| | S | GGTCCCGCTGCCATAAGAGA | (SEQ ID NO: 17) |
| | AS | GGCATCAACCCAGACAACACAA | (SEQ ID NO: 18) |
| ASL | RT | CTGCAGTGACAGCTGGTTGAGG | (SEQ ID NO: 19) |
| | S | CTGGAGCCACTGGATTCTGAG | (SEQ ID NO: 20) |
| | AS | GCCCCAAAGTTGAGTTCTGCT | (SEQ ID NO: 21) |
| ASS | RT | CCTGAGGGAATTGATGTTGATGAA | (SEQ ID NO: 22) |
| | S | CGTGGGCCGTATTGACATCGTG | (SEQ ID NO: 23) |
| | AS | CCGGTGGCATCAGTTGGCTCATA | (SEQ ID NO: 24) |
| CPS I | RT | AGGACCCGCACTGCTGGAGAAG | (SEQ ID NO: 25) |
| | S | CATCAGACTGGCTCAAAC | (SEQ ID NO: 26) |
| | AS | CAGCTGTCCTCCGAATCAC | (SEQ ID NO: 27) |
| CYP1A2 | RT | TCAGGTCGACTTTCACGCCC | (SEQ ID NO: 28) |
| | S | GGAGGCCTTCATCCTGGAGA | (SEQ ID NO: 29) |
| | AS | TCTCCCACTTGGCCAGGACT | (SEQ ID NO: 30) |
| CYP2B6 | RT | GTTGGCGGTAATGGACTGGAAGA | (SEQ ID NO: 31) |
| | S | CCCGCCCTCTGCCCCTTTTG | (SEQ ID NO: 32) |
| | AS | TCCACACTCCGCTTTCCCATCC | (SEQ ID NO: 33) |
| CYP2C9 | RT | CTCTTTCAGCCAGTGGGAAA | (SEQ ID NO: 34) |
| | S | TCCTTGTGCTCTGTCTCT | (SEQ ID NO: 35) |
| | AS | ATCCATGCAGCACCACTA | (SEQ ID NO: 36) |
| CYP2D6 | RT | GCTTCACAAAGTGGCCCTGG | (SEQ ID NO: 37) |
| | S | CCTGCGCATAGTGGTGGCTG | (SEQ ID NO: 38) |

TABLE 1-continued

Primer sequences

| Gene | | primer 5'-3' | |
|------|---|----------|---|
| | AS | GCTTCTCCCAGACGGCCTCA | (SEQ ID NO: 39) |
| | RT | AAAGAATGGATCCAAAAAATCA | (SEQ ID NO: 40) |
| CYP3A4 | S | AGTGTGGGGCTTTTATGATGG | (SEQ ID NO: 41) |
| | AS | AAGGCCTCCGGTTTGTGAAG | (SEQ ID NO: 42) |
| | RT | GGTACCATCTCTTGAATCCACC | (SEQ ID NO: 43) |
| CYP3A5 | S | TGACCCAAAGTACTGGACAG | (SEQ ID NO: 44) |
| | AS | TGAAGAAGTCCTTGCGTGTC | (SEQ ID NO: 45) |
| | RT | AGCCAAATCTACTTCCCCAGCAC | (SEQ ID NO: 46) |
| CYP3A7 | S | ATTACGCTTTGGAGGACTTCTTCT | (SEQ ID NO: 47) |
| | AS | CGTCTTCATTTCAGGGTTCTATTT | (SEQ ID NO: 48) |
| | RT | TTGGCAGAGGGGCGACGAT | (SEQ ID NO: 49) |
| GS | S | GCCTGCTTGTATGCTGGAGTC | (SEQ ID NO: 50) |
| | AS | GGCGCTACGATTGGCTACAC | (SEQ ID NO: 51) |
| | RT | AGCAGGTCCAGCAGGTTG | (SEQ ID NO: 52) |
| GSTπ | S | GCCAGAGCTGGAAGGAGG | (SEQ ID NO: 53) |
| | AS | TTCTGGGACAGCAGGGTC | (SEQ ID NO: 54) |
| | RT | CACTCCAACCCCGCCCTC | (SEQ ID NO: 55) |
| HNF4 | S | TCCGGGCTGGCATGAAGAAGG | (SEQ ID NO: 56) |
| | AS | CCAGGGGGAGCTCGCAGAAAG | (SEQ ID NO: 57) |
| | RT | CAGCTGCTGGGAAATGGTG | (SEQ ID NO: 58) |
| HNF6 | S | CCGGCCGGGAGACCTTC | (SEQ ID NO: 59) |
| | AS | AGAGTTCGACGCTGGACATC | (SEQ ID NO: 60) |
| | RT | GACGATGATGGTGAAGACAGGAG | (SEQ ID NO: 61) |
| MRP2 | S | AGCACCGACTATCCAGCATCTC | (SEQ ID NO: 62) |
| | AS | ATCCGGCCTGTGGGTGTTGTG | (SEQ ID NO: 63) |
| | RT | GTAGGTGCCATTTCCCAGAGC | (SEQ ID NO: 64) |
| NTCP | S | GGCTTTCTGCTGGGTTATGTT | (SEQ ID NO: 65) |
| | AS | GGGGAAAGAAGAAAAGTGGTC | (SEQ ID NO: 66) |
| | RT | ATCATCTCTTGGGCATTCACC | (SEQ ID NO: 67) |
| | RT | CATGTGGGGCAGCAGGGAGAAG | (SEQ ID NO: 68) |
| OTC | S | GCCGGATGCTAGTGTAACCAA | (SEQ ID NO: 69) |
| | AS | AGCCGCTTTTTCTTCTCCTCTTC | (SEQ ID NO: 70) |
| | RT | GGCAAATCCCACCAACTCCAC | (SEQ ID NO: 71) |
| PXR | S | CGCCTGCGCAAGTGCCTGGAG | (SEQ ID NO: 72) |
| | AS | GTCGGCTGGGGGTTTGTAGTTC | (SEQ ID NO: 73) |
| | RT | CCAGACCACACTTGCCCGCTATG | (SEQ ID NO: 74) |

RT, reverse transcriptase primer; S, sense PCR primer; AS, anti-sense PCR primer. AAT, α-1-antitrypsin; AFP, α-fetoprotein; ALB, albumin; Arg, arginase; ASL, argininosuccinate lyase; ASS, argininosuccinate synthetase; CK, cytokeratin; CPS, carbamoyl-phosphate synthetase; Cyp, cytochrome P450; GS, glutamine synthetase; GST, glutathione S transferase; HNF, hepatic nuclear factor; MRP, mutidrug resistance protein; NTCP, NA-dependent cholate transporting protein; OTC, ornithine transcarbamylase;; PXR, pregnane X receptor.

Characterization Human Hepatocyte Cell Lines in Monolayer

The HepaRG cells, cultured in monolayer in 24 well plates in presence and absence of DMSO as indicated above, were assessed for hepatic functions. For comparison, functions of hepatocyte cell lines NKNT-3, HepG2 and cBAL111, cultured under their respective optimal conditions, described by Hoekstra et al[18], and Deurholt[19], are given as far as determined. Results are shown in Table 2.

Table 2 shows that HepaRG cells outperformed the NKNT-3, HepG2 and cBAL111 cells in exhibiting ammonia elimination, a critical parameter in acute liver failure. Since NKNT-3 cells did not exhibit any positive metabolic parameter, the investigation of these cells was not further pursued. Comparison of the expression profiles of the HepG2, cBAL111 and HepaRG cells showed that genes expressed in highly differentiated hepatocytes, like CYPs, Arg1 and CPS were most consistently expressed in the HepaRG cells. The HepaRG cells treated with DMSO showed higher metabolic parameters compared to untreated HepaRG cells when normalized for total protein content. However the DMSO treatment killed more than 50% of the cells, as can be deduced from the lower protein/well content and also from the increased cell leakage. The absolute metabolic parameters were therefore higher when DMSO treatment was omitted in the HepaRG cells, see Table 3. Furthermore, DMSO treatment increased CYP2B6 and 3A4 expression, but other hepatic genes tested were either unaffected or decreased in their expression (Table 2).

TABLE 2

Characteristics of hepatocyte cell lines in comparison with primary human hepatocytes in monolayer.

| | NKNT-3 (reverted) | HepG2 | cBAL111 (d18) | HepaRG + DMSO | HepaRG − DMSO | PHH |
|---|---|---|---|---|---|---|
| total protein/well (μg) | 200 | 260 ± 8 | 183 ± 21 | 109 ± 21 | 247 ± 47 | 85.2 ± 30 |
| Biochemical functions | | | | | | |
| Ammonia elimination (nmol/h/mg protein) | production | undetectable | undetectable | 107 ± 41 | 72 ± 21 | 95 ± 5.0 |
| Urea production (nmol/h/mg protein) | undetectable | 3.3 ± 3.7 | 8.0 ± 6.6 | 8.1 ± 6.8 | 5.0 ± 2.0 | 96 ± 34 |
| Lactate elimination (μmol/h/mg protein) | ND | ND | ND | production | production | ND |
| Albumin production (ng/h/mg protein) | undetectable | 2.8 ± 0.3 | 8.0 ± 6.6 | ND | ND | 37.7 ± 7.7 |

TABLE 2-continued

Characteristics of hepatocyte cell lines in comparison with primary human hepatocytes in monolayer.

|  | NKNT-3 (reverted) | HepG2 | cBAL111 (d18) | HepaRG + DMSO | HepaRG − DMSO | PHH |
|---|---|---|---|---|---|---|
| ApoA1 production (µg/h/mg protein) | ND | ND | ND | 1.06 ± 0.95 | 0.78 ± 0.50 | 0.61 ± 0.16 |
| 6bOH testosteron production (nmol/h/mg protein) | ND | 0.055 ± 0.006 | ND | ND | ND | 61.7 ± 8.2 |
| mRNA levels (% of in vivo) | | | | | | |
| PXR | ND | 20 ± 8 | 11.1 | 42 ± 19 | 44 ± 16 | ND |
| HNF4 | ND | 484 ± 181 | 57.0 | 61 ± 21 | 88 ± 89 | ND |
| CYP2B6 | ND | <1 | 24.0 | 61 ± 30 | 3 ± 1 | ND |
| CYP3A4 | ND | <1 | 2.7 | 69 ± 47 | 10 ± 8 | ND |
| ALB | 24 ± 22 | 63 ± 6 | 2.0 | 23 ± 4 | 66 ± 24 | ND |
| ARG1 | ND | 11 ± 5 | 1.7 | 5 ± 4 | 15 ± 11 | ND |
| CPS | 1.3 ± 1.4 | 3 ± 1 | 5.5 | 1.1 ± 0.4 | 31 ± 19 | ND |
| GS | ND | 1564 ± 624 | 89.7 | 90 ± 29 | 214 ± 66 | ND |

(ND = not determined)
(CPS, carbamoyl phosphate synthetase; ArgI, arginase I; GS, glutamine synthetase; ArgII, Arginase II; HNF4, hepatocyte nuclear factor 4; PXR, pregnane X receptor; CYP2B6, cytochrome P450 2B6; CYP3A4, cytochromeP450 3A4; Alb, albumin)

TABLE 3

Characteristics of −DMSO and +DMSO cultures of HepaRG cells (n ≥ 10 from ≥3 independent experiments). Values are given as mean ± SD. P values refer to −DMSO vs +DMSO cultures. (ns = not significant)

|  | Parameter | −DMSO | +DMSO | P value |
|---|---|---|---|---|
| Absolute values | Total protein (µg/well) | 247 ± 47 | 109 ± 21 | <0.001 |
|  | Ammonia elimination (nmol/h) | 17.0 ± 4.6 | 11.6 ± 4.3 | <0.001 |
|  | Urea production (nmol/h) | 1.2 ± 0.5 | 0.8 ± 0.5 | 0.003 |
|  | Galactose elimination (nmol/h) | 26 ± 5.4 | 7.2 ± 1.8 | <0.001 |
|  | ApoA1 production (µg/h) | 0.17 ± 0.11 | 0.11 ± 0.11 | ns |
|  | AST leakage (mU/h) | 0.27 ± 0.07 | 0.43 ± 0.08 | <0.001 |
|  | LDH leakage (mU/h) | 1.54 ± 0.24 | 1.87 ± 0.43 | <0.001 |
| Protein normalized values | Ammonia elimination (nmol/h/mg protein) | 72 ± 21 | 107 ± 41 | <0.001 |
|  | Urea production (nmol/h/mg protein) | 5.0 ± 2.0 | 8.1 ± 6.8 | 0.02 |
|  | Galactose elimination (nmol/h/mg protein) | 100 ± 24 | 58 ± 17 | <0.001 |
|  | ApoA1 production ((µg/h/mg protein) | 0.78 ± 0.50 | 1.06 ± 0.95 | ns |
|  | AST leakage (mU/h/mg protein) | 1.3 ± 0.4 | 4.9 ± 2.4 | <0.001 |
|  | LDH leakage (mU/h/mg protein) | 7.4 ± 2.2 | 21.2 ± 9.4 | <0.001 |

Preconditioning Effect of Carbamoyl Glutamate and Conversion of Ammonia into Urea The HepaRG cells are cultured as indicated above in 24 well in presence or absence of 1 mM CG during the last 5 days. Next the cells are tested as indicated above in presence or absence of CG during 24 hours. To determine the conversion of ammonia into urea, the $^{15}N$ urea enrichment (single and double labeled) is measured in the test samples using mass-spectrometry. Similarly, HepG2 and cBAL111 cells were tested for their response to CG. Results are shown in Table 4.

TABLE 4

Urea production of HepG2, cBAL111 and HepaRG cells, cultured in monolayer.

| | Urea production | | | | $^{15}N$ urea enrichment | |
|---|---|---|---|---|---|---|
| CG Treatment | HepG2 | cBAL111 | HepaRG + DMSO | HepaRG − DMSO | HepaRG + DMSO | HepaRG − DMSO |
| −− | 1.0 ± 1.7 | undetectable | 6.0 ± 4.2 | 4.1 ± 2.2 | 15.5 ± 8.4 | 6.4 ± 4.7 |
| −+ | 1.8 ± 1.1 | 8.3 ± 8.3 | 4.9 ± 4.2 | 5.9 ± 2.4 | ND | ND |
| +− | 2.5 ± 1.4 | 10.8 ± 6.2 | 11.0 ± 5.3 | 9.6 ± 3.3 | ND | ND |
| ++ | 2.4 ± 1.6 | 9.4 ± 8.4 | 13.7 ± 4.4 | 9.5 ± 4.2 | 7.8 ± 2.4 | 24.4 ± 4.1 |

Carbamoyl glutamate (CG; 1 mM) addition was varied before and during the incubation with test medium. (−−, no CG; −+, CG only during test; +−, CG only during preincubation; ++, CG in preincubation and in testmedium). Urea production is expressed as nmol/h/mg protein and 15N urea enrichment is given as % of total urea produced. (ND = not determined)

These results show that CG treatment increases urea production more than two-fold in all cell lines. In HepaRG-DMSO cells the % of urea of the total urea produced from ammonia increased even four-fold. Furthermore pre-treatment with CG is sufficient for increasing the urea production, since the ureagenesis is similar in the +− and ++ cultures. Therefore the beneficial effects of CG on urea production are preserved even when CG is omitted from the test or during a clinical treatment. No effect of CG on other hepatic functions and the gene expression profiles were found.

EXAMPLE 2

Preparation of a Bioreactor Comprising Differentiated HepaRG Cell Cultures and Evaluation of their Metabolic and Detoxification Functionality

Large-Scale HepaRG Expansion

The cells are cultured using Hyperflasks™ (Corning) as follows. The medium is refreshed every three days. After a 2 weeks proliferation phase, at confluence, the cultures are washed twice in phosphate buffered saline and then detached by 15 min incubation in 60 ml/Hyperflask™ of Accutase™ and Accumax™ (both from Innovative Cell Technologies Inc.) in a 4:1 ratio at 37° C. The cells are harvested from the Hyperflask™ and three times washed with HepaRG medium by centrifugation at 4° C. and 3×50 g. Approximately 1.2 ml of cell pellet is harvested from one Hyperflask™. The harvested cells are used for passaging at a split ratio of 1:6 for further expansion or for loading into the AMC-BAL bioreactor. Viability is determined by trypan blue exclusion test: cells are only used to charge the AMC-BAL bioreactor if their viability exceeds 95%.

AMC-BAL Bioreactor Charging and Culturing

One liter of HepaRG medium containing 75 ml of viable HepaRG cells is injected under sterile conditions into an AMC-BAL bioreactor (cf. Flendrig et al.[15]) through three loading ports. The bioreactor is then placed in a culture cabinet at 37° C. and oxygenated with culture gas (55% $N_2$/40% $O_2$/5% $CO_2$) at a flow rate of 150 mL/min during a 3-hour attachment period. To ensure optimal cell attachment and an even cell distribution, bioreactors are rotated 340° (back and forth) along the longitudinal axis at 1 revolution/min. After this attachment period, dead and unattached cells are removed by flushing 500 mL of fresh culture medium through the bioreactor at 150 mL/min. From then on bioreactors are perfused with 1.5 L recirculating culture medium at 150 mL/min. The medium is refreshed every three days. The bioreactors are cultured in HepaRG medium for 14 days. In that period, the cells will undergo about one population doubling. The bioreactors can be continued to be cultured for at least another 3 weeks without changes in phenotype. At least one week prior to clinical application, 1 mM CG (Sigma) is added to the media to enhance the urea cycle. The bioreactors are tested every culture week and prior to clinical application for sterility and function. Laboratory model AMC-BAL bioreactors, e.g. of a different scale, are produced in essentially the same way as described above. These laboratory model bioreactors are used e.g. for clinical testing in animal models, such as rats with acute liver failure.

Sterility Test

Culture medium perfused for three days through the bioreactor is assessed for sterility by the tests summarized in the below Table 5.

TABLE 5

Sterility tests for bioartificial liver application

| TEST | METHOD | ACCEPTANCE CRITERIA |
|---|---|---|
| Bacteria | Bacterial DNA (PCR) | Negative |
|  | Standard culture | <5 CFU/ml |
| Mycoplasma | DNA PCR | negative |
| Fungi | Standard culture | <5 CFU/ml |

Tests of AMC-BAL Functionality

The purpose of this test is to monitor the bioreactor culture and to assess the quality of the hepatocytes in the bioreactors prior to clinical application. These tests are performed once a week.

Firstly, small pieces of matrix (T-bags; 3 per time point) are withdrawn from the bioreactor. These matrices allow the harvesting of cells from the bioreactor, see Poyck et al.[16]. The matrices are collected in 1 ml of Trizol (GibcoBRL). Subsequently RNA is isolated according to the instructions of the manufacturer. Next, levels of mRNAs of hepatic genes and 18S rRNA are quantified by RT-PCR.

Secondly, oxygen consumption is determined by measuring the decrease in oxygen tension during the first 15 min after closure of the oxygen supply to the bioreactor as described by Van de Kerkhove et al[20].

Thirdly, the culture medium is replaced by 1500 ml test medium. The hepatocytes in the AMC-BAL bioreactors are exposed to a recirculating iso-osmotic test medium for 24 hours, containing HepaRG medium (−DMSO) with different substrates (1.5 mM $^{15}NH_4Cl$, 125 µM testosterone and 2.75 mM galactose) together with 2 mM lactate. At first 700 ml test medium is flushed through the bioreactor followed by recirculation of 800 ml test medium during 24 hours. At t=0 (test medium before connection to the bioreactor), t=30', 60', 120', 180', 8 hrs and 24 hrs a 1 mL sample is taken and analysed for substrate (ammonia, testosterone, lactate, glucose) and product (urea, apoA1, albumin) concentration as well as cell damage (AST, aspartate-amino transferase and LDH, lactate dehydrogenase). From the changes in concentration an activity per hour and per billion cells seeded is calculated. Quality of the cell-loaded bioreactors, measured by hepatocyte function at the start of the treatment, is compared with values of bioreactors charged with primary hepatocytes that have been tested extensively in vitro and in vivo in the past.

Table 6 shows the comparison between the HepaRG cells cultured in monolayer for 30 days with/without 2% DMSO added during the last 15 days (method according to patent US 2005/0064594) and HepaRG cells cultured in a laboratory model AMC-BAL bioreactors (10 mL internal volume) loaded with a suspension containing 2 mL HepaRG cell pellet and cultured for 13 days in absence of DMSO, but in presence of 1 mM CG.

These data indicate that the new culture method (in AMC-BAL bioreactor+CG−DMSO) improves hepatic differentiation markedly compared to the initial culture conditions (monolayer, −CG, either with or without DMSO); the urea production, conversion of ammonia into urea, and transcript levels of CPS, ArgI, GS, HNF4 and Alb are significantly improved.

TABLE 6

Effects of bioreactor culturing including CG addition and absence of DMSO on the functionality of HepaRG cells, compared to monolayer cultures. *= P < 0.05.

| | Functionality per culture system | | | % improvement by bioreactor versus | |
|---|---|---|---|---|---|
| | Monolayer + DMSO − CG | Monolayer − DMSO − CG | Bioreactor − DMSO + CG | Monolayer + DMSO − CG | Monolayer − DMSO − CG |
| Ammonia elimination (nmol/h/mg protein) | 110 ± 49 | 66.0 ± 28.0 | 143 ± 105 | 134 | 199* |
| Urea production (nmol/h/mg protein) | 7.0 ± 7.0 | 5.0 ± 2.0 | 13.1 ± 1.2 | 187* | 262* |
| 15N urea enrichment (% of total urea) | 16.0 ± 8.4 | 6.0 ± 4.7 | 25.1 ± 3.7 | 157* | 418* |
| Lactate consumption (nmol/h/mg protein) | production | production | 42.1 ± 14.7 | conversion* | conversion* |
| ApoA1 synthesis (ug/h/mg protein) | 1.2 ± 1.1 | 0.78 ± 0.50 | 1.2 ± 0.9 | 113 | 154 |
| CPS mRNA level (% of in vivo) | 1.1 ± 0.4 | 30.5 ± 19.1 | 44.1 ± 32.2 | 4000* | 145 |
| ArgI mRNA level (% of in vivo) | 4.6 ± 3.7 | 14.8 ± 11.3 | 22.9 ± 10.4 | 460* | 155 |
| GS mRNA level (% of in vivo) | 90.1 ± 29.1 | 214 ± 66.1 | 643 ± 395 | 714 | 300* |
| ArgII mRNA level (% of in vivo) | 718 ± 463 | 570 ± 364 | 305 ± 143 | 42 | 54 |
| HNF4 mRNA level (% of in vivo) | 60.8 ± 21.1 | 88.3 ± 89 | 386 ± 216 | 198* | 187* |
| PXR mRNA level (% of in vivo) | 41.7 ± 19.2 | 44.1 ± 16.4 | 82.5 ± 68.9 | 633 | 437 |
| CYP2B6 mRNA level (% of in vivo) | 60.7 ± 30.0 | 3.5 ± 1.3 | 30.2 ± 15.9 | 49 | 863* |
| CYP3A4 mRNA level (% of in vivo) | 68.9 ± 47.2 | 9.6 ± 8.2 | 102 ± 49.4 | 148 | 1063* |
| Alb mRNA level (% of in vivo) | 22.7 ± 4.4 | 66.4 ± 24.3 | 72.1 ± 26.0 | 313* | 109 |

(CPS, carbamoyl phosphate synthetase; ArgI, arginase I, GS, glutamine synthetase; ArgII, Arginase II; HNF4, hepatocyte nuclear factor 4; PXR, pregnane X receptor; CYP2B6, cytochrome P450 2B6; CYP3A4, cytochromeP450 3A4; Alb, albumin)

EXAMPLE 3

Operating Procedure of Application of the Bioartificial Liver

The charged and tested AMC-BAL bioreactor, as described in example 1, is flushed by an electrolyte solution (Schiwa) to wash out test- and culture medium and transported while stored on ice to the medical centre in demand of the bioreactor. The charged bioreactor is connected to the patient within 4 hours.

Extra-corporeal hemodialysis and plasmapheresis are standard procedures at Intensive Cares (IC). The BAL system (see FIG. 1) consists of a plasma circuit including the bioreactor and a blood circuit incorporating a plasma-separator. Blood is pumped (50 ml/min) from the veno-venous or arterio-venous catheters to the plasma separator (Braun-Carex Diapact CRRT). This system enables continuous plasmapheresis for a period of 12 hours, after which the disposable needs to be replaced. The plasmafilter is Hemaplex BT 900/A 0.2 m². The plasma perfuses then through the bioreactor.

Between the bioreactor and the return-plasma line to the patient two filters are inserted: one filter is a polyester cell filter (leucocyte polyester filter) and the second one serially placed is a 0.2 micron filter, surface 0.1 m², to remove cells or liver cell debris. A high flow plasma loop (normally at 150 ml/min) is introduced to control the plasma flow inside the bioreactors. After recirculation through the bioreactor, the treated plasma is reunited with the blood cells from the plasma-separator and returned to the patient. The BAL-system has a total extracorporeal volume of 950 ml. The BAL-Incubator and tubing sets are custom made of standard dialysis components (RAND, Mirandola, Italy). A computerised pressure monitoring system is included to check the condition of the two plasma filters regarding membrane plugging and fouling. Additional safety features involved controls for gas flow, temperature, and balanced plasma exchange.

The used Diapact CRRT plasmapheresis device has been qualified according to IEC 513, IEC 529, EN 60601-1, prEN 1441, IEC 601-1-4. IEC 601-2-16, EN 60601-1-2.

The plasmapheresis device is mounted according to the manufacturers instructions with the recommended sterile tubing set and hollow fibre plasmapheresis filter Hemaplex BT 900/A 0.2 m².

The system is primed with physiological saline and air bubbles are removed.

The patient is connected to the monitor: ECG and arterial pressure are monitored automatically. After iodation of the skin a veno-venous catheter is inserted by the physician in a cubital or femoral vein. If no venous access can be obtained the femoral artery will be used.

Plasma flow from the patient is 30-40 ml/min. Plasma flow across the bioreactor will be normally about 150 ml/min.

If plasmapheresis by plasma filtration (mostly 0.5 micron pore diameter) is used no extra filter is needed in the plasma inflow circuit to the bioreactor (see appendix 1). Sufficient anticoagulation will be obtained by infusion of low molecular weight heparin. After connecting the patient to the plasmapheresis circuit, an observation period of at least one hour of stable haemodynamics is required before the bioreactor is inserted in the circuit. Plasmapheresis is continuous for periods of maximally 12 hours, interrupted by a plasmapheresis free period of another 12 hours. If necessary the BAL is refreshed by a new one.

References

1: Park and Lee, "Bioartificial Liver Systems: Current Status and Future Perspective"; J. Biosci. Bioeng 2005; Vol. 99, No. 4, 311-319
2: Sgroi et al., "What clinical alternatives to whole liver transplantation? Current status of artificial devices and hepatocyte transplantation"; Transplantation 2009; 87(4): 457-466.
3: Poyck et al., "Evaluation of a new immortalized human fetal liver cell line (cBAL111) for application in a bioartificial liver", J. Hepatol. 2007; 48(2), 266-275
4: Nyberg et al., "Primary hepatocytes outperform Hep G2 cells as the source of biotransformation functions in a bioartificial liver", Ann Surg. 1994; 220(1), 59-67

5: Wang et al., "The Bioreactor With CYP3A4- and Glutamine Synthetase-Introduced HepG2 Cells: Treatment of Hepatic Failure Dog With Diazepam Overdosage", Artif Organs. 2005; 29(8), 681-684

6: Enosawa et al., "The significant improvement of survival times and pathological parameters by bioartificial liver with recombinant HepG2 in porcine liver failure model", Cell Transplant 2006; 15(10), 873-80

7: Takahashi et al. "Double-compartment cell culture apparatus: construction and biochemical evaluation for bioartificial liver support", Cell Transplant 2006; 15(10), 945-952

8: Mavri-Damelin et al. "Cells for bioartificial liver devices: the human hepatoma derived cell line C3A produces urea but does not detoxify ammonia", Biotechnol. Bioeng. 2008; 99(3), 644-51

9: Kosuge et al. "A comprehensive gene expression analysis of human hepatocellular carcinoma cell lines as components of a bioartificial liver using a radial flow bioreactor", Liver Int. 2007; 27(1), 101-108

10: Kanai et al., "Extracorporeal bioartificial liver using the radial-flow bioreactor in treatment of fetal experimental hepatic encephalopathy", Artif. Organs 2007; 31(2), 148-151

11: Saito et al. "Reconstruction of liver organoid using a bioreactor", World J. Gastroenterol. 2006; 12(12), 1881-1888

12: Hoekstra et al., "Increased reproducibility of quantitative reverse trancriptase-PCR", Anal. Biochem. 2005; Vol 340, 376-379

13: V. d. Kerkhove et al., "Phase I clinical trial with the AMC-bioartificial liver", Int J Artif Organs. 2002; 25(10), 950-9

14: Rozga et al., "Development and testing of a bioartificial liver", The Hepatocyte Review 2002, 543-560

15: Flendrig et al., "In vitro evaluation of a novel bioreactor based on an integral oxygenator and a spirally wound nonwoven polyester matrix for hepatocyte culture as small aggregates", J. Hepatol. 1997; 26, 1379-1392

16: Poyck et al., "Time-related analysis of metabolic liver functions, cellular morphology and gene expression of hepatocytes in the AMC-BAL", Tissue Eng. 2007; 13, 1235-1246

17: Ramakers et al., "Assumption-free analysis of quantitative real-time polymerase chain reaction (PCR) data" Neurosci. Lett. 2003; 339, 62-66

18: Hoekstra et al., "Assessment of in vitro applicability of reversibly immortalized NKNT-3 cells and clonal derivatives" Cell Transplant. 2006; 15, 423-33.

19: Deurholt et al., "Novel immortalized Human Fetal Liver Cell Line, cBAL111, has the potential to fully differentiate into functional hepatocytes" BMC Biotechnology 2009, 9, 89

20: Van de Kerkhove et al., "Assessment and improvement of liver specific function of the AMC-bioartificial liver. Int. J. Artif. Organs, 2005; 28, 617-30.

The invention claimed is:

1. A cell culture comprising differentiated cells from a human hepatocyte cell line in a suitable culture medium, wherein said differentiated cells have constitutive liver-specific metabolic activity, the cell culture obtained by a process comprising:
   selecting a human hepatocyte cell line;
   a phase of cell proliferation comprising culturing the cells of said human hepatocyte cell line in a suitable culture medium; and
   a phase of cell differentiation comprising culturing the cells in a suitable culture medium comprising at least 0.5 mM carbamoyl glutamate.

2. The cell culture according to claim 1, wherein in the phase of cell proliferation the cells are cultured on a three-dimensional support matrix in said suitable culture medium.

3. The cell culture according to claim 1, wherein in the phase of cell differentiation said suitable culture medium is substantially free of DMSO.

4. The cell culture according to claim 3, wherein in the phase of cell differentiation said suitable culture medium comprises less than 0.1% DMSO.

5. The cell culture according to claim 1, wherein in the phase of cell differentiation the cells are cultured in said suitable culture medium comprising at least 0.5 mM carbamoyl glutamate for at least 5 days.

6. A process of producing a cell culture, comprising:
   selecting a human hepatocyte cell line;
   a phase of cell proliferation comprising culturing the cells of said human hepatocyte cell line in a suitable culture medium; and
   a phase of cell differentiation comprising culturing the cells in a suitable culture medium comprising at least 0.5 mM carbamoyl glutamate.

7. The process according to claim 6, wherein in the phase of cell proliferation the cells are cultured in monolayer or in suspension in said suitable culture medium.

8. The process according to claim 6, wherein the cells are grown and/or differentiated on a three-dimensional support matrix in said suitable culture medium.

9. The process according to claim 6, further comprising in between the cell proliferation and cell differentiation phases:
   loading viable cells to an amount of at least 5% of normal liver mass in a bioreactor comprising a three dimensional support matrix, and allowing the cells to attach to said matrix; and
   culturing the cells in the bioreactor in said suitable culture medium to achieve at least one population doubling.

10. The process according to claim 6, wherein in the phase of cell differentiation said suitable culture medium is substantially free of DMSO.

11. The process according to claim 6, wherein in the phase of cell differentiation the cells are cultured in said suitable culture medium comprising at least 0.5 mM carbamoyl glutamate for at least 5 days.

12. The process according to 6, wherein in the phase of cell differentiation said suitable culture medium comprises less than 0.1% DMSO.

* * * * *

SEQUENCE LISTING

```
<160> NUMBER OF SEQ ID NOS: 74

<210> SEQ ID NO 1
<211> LENGTH: 19
<212> TYPE: DNA
<213> ORGANISM: Artificial
<220> FEATURE:
<223> OTHER INFORMATION: primer

<400> SEQUENCE: 1
gcatcgccgg tcggcatcg                                                19

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
ttcggaactg aggccatgat                                               20

<210> SEQ ID NO 3
<211> LENGTH: 21
<212> TYPE: DNA
<213> ORGANISM: Artificial
<220> FEATURE:
<223> OTHER INFORMATION: primer

<400> SEQUENCE: 3
cgaacctccg actttcgttc t                                             21

<210> SEQ ID NO 4
<211> LENGTH: 21
<212> TYPE: DNA
<213> ORGANISM: Artificial
```

<220> FEATURE:
<223> OTHER INFORMATION: primer

<400> SEQUENCE: 4
gggggataga catgggtatg g                                    21

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
acagaaggtc tgccagcttc                                      20

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
gatggtcagc acagccttat                                      20

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
cgttttgtct tctcttcccc                                      20

<210> SEQ ID NO 8
<211> LENGTH: 19
<212> TYPE: DNA
<213> ORGANISM: Artificial
<220> FEATURE:
<223> OTHER INFORMATION: primer

<400> SEQUENCE: 8
tkccaacagg aggcyatgc                                       19

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
cccaaagcak cacgagtttt                                      20

<210> SEQ ID NO 10
<211> LENGTH: 25
<212> TYPE: DNA
<213> ORGANISM: Artificial
<220> FEATURE:
<223> OTHER INFORMATION: primer

<400> SEQUENCE: 10
acttccagag ctgaaaagca tggtc                                25

```
<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
tgagcagctt ggagagtaca                                                 20

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
gttcaggacc acggatagat                                                 20

<210> SEQ ID NO 13
<211> LENGTH: 24
<212> TYPE: DNA
<213> ORGANISM: Artificial
<220> FEATURE:
<223> OTHER INFORMATION: primer

<400> SEQUENCE: 13
tgtgattacc ctcccgagca agtc                                            24

<210> SEQ ID NO 14
<211> LENGTH: 23
<212> TYPE: DNA
<213> ORGANISM: Artificial
<220> FEATURE:
<223> OTHER INFORMATION: primer

<400> SEQUENCE: 14
ttggcaaggt gatggaagaa aca                                             23

<210> SEQ ID NO 15
<211> LENGTH: 23
<212> TYPE: DNA
<213> ORGANISM: Artificial
<220> FEATURE:
<223> OTHER INFORMATION: primer

<400> SEQUENCE: 15
cctcccgagc aagtccgaaa caa                                             23

<210> SEQ ID NO 16
<211> LENGTH: 24
<212> TYPE: DNA
<213> ORGANISM: Artificial
<220> FEATURE:
<223> OTHER INFORMATION: primer

<400> SEQUENCE: 16
acaagggcag aaaagaaaag gagt                                            24

<210> SEQ ID NO 17
<211> LENGTH: 20
<212> TYPE: DNA
<213> ORGANISM: Artificial
<220> FEATURE:
<223> OTHER INFORMATION: primer
```

<400> SEQUENCE: 17
ggtcccgctg ccataagaga                                          20

<210> SEQ ID NO 18
<211> LENGTH: 22
<212> TYPE: DNA
<213> ORGANISM: Artificial
<220> FEATURE:
<223> OTHER INFORMATION: primer

<400> SEQUENCE: 18
ggcatcaacc cagacaacac aa                                       22

<210> SEQ ID NO 19
<211> LENGTH: 22
<212> TYPE: DNA
<213> ORGANISM: Artificial
<220> FEATURE:
<223> OTHER INFORMATION: primer

<400> SEQUENCE: 19
ctgcagtgac agctggttga gg                                       22

<210> SEQ ID NO 20
<211> LENGTH: 21
<212> TYPE: DNA
<213> ORGANISM: Artificial
<220> FEATURE:
<223> OTHER INFORMATION: primer

<400> SEQUENCE: 20
ctggagccac tggattctga g                                        21

<210> SEQ ID NO 21
<211> LENGTH: 21
<212> TYPE: DNA
<213> ORGANISM: Artificial
<220> FEATURE:
<223> OTHER INFORMATION: primer

<400> SEQUENCE: 21
gccccaaagt tgagttctgc t                                        21

<210> SEQ ID NO 22
<211> LENGTH: 24
<212> TYPE: DNA
<213> ORGANISM: Artificial
<220> FEATURE:
<223> OTHER INFORMATION: primer

<400> SEQUENCE: 22
cctgagggaa ttgatgttga tgaa                                     24

<210> SEQ ID NO 23
<211> LENGTH: 22
<212> TYPE: DNA
<213> ORGANISM: Artificial
<220> FEATURE:
<223> OTHER INFORMATION: primer

<400> SEQUENCE: 23
cgtgggccgt attgacatcg tg                                       22

<210> SEQ ID NO 24

<211> LENGTH: 23
<212> TYPE: DNA
<213> ORGANISM: Artificial
<220> FEATURE:
<223> OTHER INFORMATION: primer

<400> SEQUENCE: 24
ccggtggcat cagttggctc ata                                           23

<210> SEQ ID NO 25
<211> LENGTH: 22
<212> TYPE: DNA
<213> ORGANISM: Artificial
<220> FEATURE:
<223> OTHER INFORMATION: primer

<400> SEQUENCE: 25
aggacccgca ctgctggaga ag                                            22

<210> SEQ ID NO 26
<211> LENGTH: 18
<212> TYPE: DNA
<213> ORGANISM: Artificial
<220> FEATURE:
<223> OTHER INFORMATION: primer

<400> SEQUENCE: 26
catcagactg gctcaaac                                                 18

<210> SEQ ID NO 27
<211> LENGTH: 19
<212> TYPE: DNA
<213> ORGANISM: Artificial
<220> FEATURE:
<223> OTHER INFORMATION: primer

<400> SEQUENCE: 27
cagctgtcct ccgaatcac                                                19

<210> SEQ ID NO 28
<211> LENGTH: 20
<212> TYPE: DNA
<213> ORGANISM: Artificial
<220> FEATURE:
<223> OTHER INFORMATION: primer

<400> SEQUENCE: 28
tcaggtcgac tttcacgccc                                               20

<210> SEQ ID NO 29
<211> LENGTH: 20
<212> TYPE: DNA
<213> ORGANISM: Artificial
<220> FEATURE:
<223> OTHER INFORMATION: primer

<400> SEQUENCE: 29
ggaggccttc atcctggaga                                               20

<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30

-continued

```
tctcccactt ggccaggact                                              20

<210> SEQ ID NO 31
<211> LENGTH: 23
<212> TYPE: DNA
<213> ORGANISM: Artificial
<220> FEATURE:
<223> OTHER INFORMATION: primer

<400> SEQUENCE: 31
gttggcggta atggactgga aga                                          23

<210> SEQ ID NO 32
<211> LENGTH: 20
<212> TYPE: DNA
<213> ORGANISM: Artificial
<220> FEATURE:
<223> OTHER INFORMATION: primer

<400> SEQUENCE: 32
cccgccctct gcccctttg                                               20

<210> SEQ ID NO 33
<211> LENGTH: 22
<212> TYPE: DNA
<213> ORGANISM: Artificial
<220> FEATURE:
<223> OTHER INFORMATION: primer

<400> SEQUENCE: 33
tccacactcc gctttcccat cc                                           22

<210> SEQ ID NO 34
<211> LENGTH: 20
<212> TYPE: DNA
<213> ORGANISM: Artificial
<220> FEATURE:
<223> OTHER INFORMATION: primer

<400> SEQUENCE: 34
ctctttcagc cagtgggaaa                                              20

<210> SEQ ID NO 35
<211> LENGTH: 18
<212> TYPE: DNA
<213> ORGANISM: Artificial
<220> FEATURE:
<223> OTHER INFORMATION: primer

<400> SEQUENCE: 35
tccttgtgct ctgtctct                                                18

<210> SEQ ID NO 36
<211> LENGTH: 18
<212> TYPE: DNA
<213> ORGANISM: Artificial
<220> FEATURE:
<223> OTHER INFORMATION: primer

<400> SEQUENCE: 36
atccatgcag caccacta                                                18

<210> SEQ ID NO 37
<211> LENGTH: 20
<212> TYPE: DNA
```

-continued

```
<213> ORGANISM: Artificial
<220> FEATURE:
<223> OTHER INFORMATION: primer

<400> SEQUENCE: 37
gcttcacaaa gtggccctgg                                               20

<210> SEQ ID NO 38
<211> LENGTH: 20
<212> TYPE: DNA
<213> ORGANISM: Artificial
<220> FEATURE:
<223> OTHER INFORMATION: primer

<400> SEQUENCE: 38
cctgcgcata gtggtggctg                                               20

<210> SEQ ID NO 39
<211> LENGTH: 20
<212> TYPE: DNA
<213> ORGANISM: Artificial
<220> FEATURE:
<223> OTHER INFORMATION: primer

<400> SEQUENCE: 39
gcttctccca gacggcctca                                               20

<210> SEQ ID NO 40
<211> LENGTH: 22
<212> TYPE: DNA
<213> ORGANISM: Artificial
<220> FEATURE:
<223> OTHER INFORMATION: primer

<400> SEQUENCE: 40
aaagaatgga tccaaaaaat ca                                            22

<210> SEQ ID NO 41
<211> LENGTH: 21
<212> TYPE: DNA
<213> ORGANISM: Artificial
<220> FEATURE:
<223> OTHER INFORMATION: primer

<400> SEQUENCE: 41
agtgtggggc ttttatgatg g                                             21

<210> SEQ ID NO 42
<211> LENGTH: 20
<212> TYPE: DNA
<213> ORGANISM: Artificial
<220> FEATURE:
<223> OTHER INFORMATION: primer

<400> SEQUENCE: 42
aaggcctccg gtttgtgaag                                               20

<210> SEQ ID NO 43
<211> LENGTH: 22
<212> TYPE: DNA
<213> ORGANISM: Artificial
<220> FEATURE:
<223> OTHER INFORMATION: primer

<400> SEQUENCE: 43
ggtaccatct cttgaatcca cc                                            22
```

```
<210> SEQ ID NO 44
<211> LENGTH: 20
<212> TYPE: DNA
<213> ORGANISM: Artificial
<220> FEATURE:
<223> OTHER INFORMATION: primer

<400> SEQUENCE: 44
tgacccaaag tactggacag                                                   20

<210> SEQ ID NO 45
<211> LENGTH: 20
<212> TYPE: DNA
<213> ORGANISM: Artificial
<220> FEATURE:
<223> OTHER INFORMATION: primer

<400> SEQUENCE: 45
tgaagaagtc cttgcgtgtc                                                   20

<210> SEQ ID NO 46
<211> LENGTH: 23
<212> TYPE: DNA
<213> ORGANISM: Artificial
<220> FEATURE:
<223> OTHER INFORMATION: primer

<400> SEQUENCE: 46
agccaaatct acttccccag cac                                               23

<210> SEQ ID NO 47
<211> LENGTH: 24
<212> TYPE: DNA
<213> ORGANISM: Artificial
<220> FEATURE:
<223> OTHER INFORMATION: primer

<400> SEQUENCE: 47
attacgcttt ggaggacttc ttct                                              24

<210> SEQ ID NO 48
<211> LENGTH: 24
<212> TYPE: DNA
<213> ORGANISM: Artificial
<220> FEATURE:
<223> OTHER INFORMATION: primer

<400> SEQUENCE: 48
cgtcttcatt tcagggttct attt                                              24

<210> SEQ ID NO 49
<211> LENGTH: 19
<212> TYPE: DNA
<213> ORGANISM: Artificial
<220> FEATURE:
<223> OTHER INFORMATION: primer

<400> SEQUENCE: 49
ttggcagagg ggcgacgat                                                    19

<210> SEQ ID NO 50
<211> LENGTH: 21
<212> TYPE: DNA
<213> ORGANISM: Artificial
<220> FEATURE:
```

```
<223> OTHER INFORMATION: primer

<400> SEQUENCE: 50
gcctgcttgt atgctggagt c                                              21

<210> SEQ ID NO 51
<211> LENGTH: 20
<212> TYPE: DNA
<213> ORGANISM: Artificial
<220> FEATURE:
<223> OTHER INFORMATION: primer

<400> SEQUENCE: 51
ggcgctacga ttggctacac                                                20

<210> SEQ ID NO 52
<211> LENGTH: 18
<212> TYPE: DNA
<213> ORGANISM: Artificial
<220> FEATURE:
<223> OTHER INFORMATION: primer

<400> SEQUENCE: 52
agcaggtcca gcaggttg                                                  18

<210> SEQ ID NO 53
<211> LENGTH: 18
<212> TYPE: DNA
<213> ORGANISM: Artificial
<220> FEATURE:
<223> OTHER INFORMATION: primer

<400> SEQUENCE: 53
gccagagctg gaaggagg                                                  18

<210> SEQ ID NO 54
<211> LENGTH: 18
<212> TYPE: DNA
<213> ORGANISM: Artificial
<220> FEATURE:
<223> OTHER INFORMATION: primer

<400> SEQUENCE: 54
ttctgggaca gcagggtc                                                  18

<210> SEQ ID NO 55
<211> LENGTH: 19
<212> TYPE: DNA
<213> ORGANISM: Artificial
<220> FEATURE:
<223> OTHER INFORMATION: primer

<400> SEQUENCE: 55
cactccaacc ccgcccctc                                                 19

<210> SEQ ID NO 56
<211> LENGTH: 21
<212> TYPE: DNA
<213> ORGANISM: Artificial
<220> FEATURE:
<223> OTHER INFORMATION: primer

<400> SEQUENCE: 56
tccgggctgg catgaagaag g                                              21
```

```
<210> SEQ ID NO 57
<211> LENGTH: 21
<212> TYPE: DNA
<213> ORGANISM: Artificial
<220> FEATURE:
<223> OTHER INFORMATION: primer

<400> SEQUENCE: 57 ccaggggggag ctcgcagaaa g                                              21

<210> SEQ ID NO 58
<211> LENGTH: 19
<212> TYPE: DNA
<213> ORGANISM: Artificial
<220> FEATURE:
<223> OTHER INFORMATION: primer

<400> SEQUENCE: 58
cagctgctgg gaaatggtg                                                  19

<210> SEQ ID NO 59
<211> LENGTH: 17
<212> TYPE: DNA
<213> ORGANISM: Artificial
<220> FEATURE:
<223> OTHER INFORMATION: primer

<400> SEQUENCE: 59
ccggccggga gaccttc                                                    17

<210> SEQ ID NO 60
<211> LENGTH: 20
<212> TYPE: DNA
<213> ORGANISM: Artificial
<220> FEATURE:
<223> OTHER INFORMATION: primer

<400> SEQUENCE: 60
agagttcgac gctggacatc                                                 20

<210> SEQ ID NO 61
<211> LENGTH: 23
<212> TYPE: DNA
<213> ORGANISM: Artificial
<220> FEATURE:
<223> OTHER INFORMATION: primer

<400> SEQUENCE: 61
gacgatgatg gtgaagacag gag                                             23

<210> SEQ ID NO 62
<211> LENGTH: 22
<212> TYPE: DNA
<213> ORGANISM: Artificial
<220> FEATURE:
<223> OTHER INFORMATION: primer

<400> SEQUENCE: 62
agcaccgact atccagcatc tc                                              22

<210> SEQ ID NO 63
<211> LENGTH: 21
<212> TYPE: DNA
<213> ORGANISM: Artificial
<220> FEATURE:
<223> OTHER INFORMATION: primer
```

```
<400> SEQUENCE: 63
atccggcctg tgggtgttgt g                                              21

<210> SEQ ID NO 64
<211> LENGTH: 21
<212> TYPE: DNA
<213> ORGANISM: Artificial
<220> FEATURE:
<223> OTHER INFORMATION: primer

<400> SEQUENCE: 64
gtaggtgcca tttcccagag c                                              21

<210> SEQ ID NO 65
<211> LENGTH: 21
<212> TYPE: DNA
<213> ORGANISM: Artificial
<220> FEATURE:
<223> OTHER INFORMATION: primer

<400> SEQUENCE: 65
ggctttctgc tgggttatgt t                                              21

<210> SEQ ID NO 66
<211> LENGTH: 21
<212> TYPE: DNA
<213> ORGANISM: Artificial
<220> FEATURE:
<223> OTHER INFORMATION: primer

<400> SEQUENCE: 66
ggggaaagaa gaaaagtggt c                                              21

<210> SEQ ID NO 67
<211> LENGTH: 21
<212> TYPE: DNA
<213> ORGANISM: Artificial
<220> FEATURE:
<223> OTHER INFORMATION: primer

<400> SEQUENCE: 67
atcatctctt gggcattcac c                                              21

<210> SEQ ID NO 68
<211> LENGTH: 22
<212> TYPE: DNA
<213> ORGANISM: Artificial
<220> FEATURE:
<223> OTHER INFORMATION: primer

<400> SEQUENCE: 68
catgtggggc agcagggaga ag                                             22

<210> SEQ ID NO 69
<211> LENGTH: 21
<212> TYPE: DNA
<213> ORGANISM: Artificial
<220> FEATURE:
<223> OTHER INFORMATION: primer

<400> SEQUENCE: 69
gccggatgct agtgtaacca a                                              21

<210> SEQ ID NO 70
<211> LENGTH: 23
```

```
<212> TYPE: DNA
<213> ORGANISM: Artificial
<220> FEATURE:
<223> OTHER INFORMATION: primer

<400> SEQUENCE: 70
agccgctttt tcttctcctc ttc                                         23

<210> SEQ ID NO 71
<211> LENGTH: 21
<212> TYPE: DNA
<213> ORGANISM: Artificial
<220> FEATURE:
<223> OTHER INFORMATION: primer

<400> SEQUENCE: 71
ggcaaatccc accaactcca c                                           21

<210> SEQ ID NO 72
<211> LENGTH: 21
<212> TYPE: DNA
<213> ORGANISM: Artificial
<220> FEATURE:
<223> OTHER INFORMATION: primer

<400> SEQUENCE: 72
cgcctgcgca agtgcctgga g                                           21

<210> SEQ ID NO 73
<211> LENGTH: 22
<212> TYPE: DNA
<213> ORGANISM: Artificial
<220> FEATURE:
<223> OTHER INFORMATION: primer

<400> SEQUENCE: 73
gtcggctggg ggtttgtagt tc                                          22

<210> SEQ ID NO 74
<211> LENGTH: 23
<212> TYPE: DNA
<213> ORGANISM: Artificial
<220> FEATURE:
<223> OTHER INFORMATION: primer

<400> SEQUENCE: 74
ccagaccaca cttgcccgct atg                                         23
```